United States Patent
Griffith et al.

(10) Patent No.: US 11,007,206 B2
(45) Date of Patent: *May 18, 2021

(54) CYCLIC BORONIC ACID ESTER DERIVATIVES AND THERAPEUTIC USES THEREOF

(71) Applicant: Melinta Subsidiary Corp., Morristown, NJ (US)

(72) Inventors: David C. Griffith, San Marcos, CA (US); Michael N. Dudley, San Diego, CA (US); Olga Lomovskaya, Mill Valley, CA (US)

(73) Assignee: MELINTA SUBSIDIARY CORP., Morristown, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/746,574

(22) Filed: Jan. 17, 2020

(65) Prior Publication Data

US 2020/0147111 A1    May 14, 2020

Related U.S. Application Data

(63) Continuation of application No. 13/843,579, filed on Mar. 15, 2013, now Pat. No. 10,561,675.
(Continued)

(51) Int. Cl.
| | |
|---|---|
| *A61K 31/69* | (2006.01) |
| *A61K 31/00* | (2006.01) |
| *A61K 31/4196* | (2006.01) |
| *A61K 45/06* | (2006.01) |
| *A61K 31/407* | (2006.01) |
| *A61K 31/403* | (2006.01) |

(52) U.S. Cl.
CPC ............ *A61K 31/69* (2013.01); *A61K 31/403* (2013.01); *A61K 31/407* (2013.01); *A61K 31/4196* (2013.01); *A61K 45/06* (2013.01); *Y02A 50/30* (2018.01)

(58) Field of Classification Search
CPC ..... A61K 31/69; A61K 31/40; A61K 31/4196
USPC .............................................. 514/64, 210.12
See application file for complete search history.

(56) References Cited

U.S. PATENT DOCUMENTS

| 4,194,047 A | 3/1980 | Christensen et al. |
| 4,260,543 A | 4/1981 | Miller |
(Continued)

FOREIGN PATENT DOCUMENTS

| EP | 1550657 A1 | 7/2005 |
| JP | 2003229277 A | 8/2003 |
(Continued)

OTHER PUBLICATIONS

International Preliminary Report on Patentability dated Dec. 18, 2014 for International Patent Application No. PCT/US2013/044377, filed Jun. 5, 2013.
(Continued)

*Primary Examiner* — Shengjun Wang
(74) *Attorney, Agent, or Firm* — Wilmer Cutler Pickering; Hale and Dorr LLP

(57) ABSTRACT

Method of treating or ameliorating a bacterial infection comprising administering a composition comprising a cyclic boronic acid ester compound in combination with a carbapenem antibacterial agent such as Biapenem, and the pharmacokinetics studies thereof are provided.

20 Claims, 6 Drawing Sheets

Related U.S. Application Data

(60) Provisional application No. 61/656,452, filed on Jun. 6, 2012.

(56) References Cited

U.S. PATENT DOCUMENTS

| | | | |
|---|---|---|---|
| 4,409,214 | A | 10/1983 | Takaya et al. |
| 4,822,786 | A | 4/1989 | Zama et al. |
| 5,888,998 | A | 3/1999 | Maiti et al. |
| 6,184,363 | B1 | 2/2001 | Shoichet et al. |
| 6,586,615 | B1 | 7/2003 | Kettner et al. |
| 7,271,186 | B1 | 9/2007 | Shoichet et al. |
| 7,439,253 | B2 | 10/2008 | Lampilas et al. |
| 7,582,621 | B2 | 9/2009 | Baker et al. |
| 7,612,087 | B2 | 11/2009 | Aszodi et al. |
| 8,680,136 | B2 | 3/2014 | Hirst et al. |
| 9,012,491 | B2 | 4/2015 | Reddy et al. |
| 10,172,874 | B2 | 1/2019 | Hirst et al. |
| 10,183,034 | B2 | 1/2019 | Hirst et al. |
| 10,561,675 | B2 * | 2/2020 | Griffith ............ A61K 45/06 |
| 2004/0019203 | A1 | 1/2004 | Micetich et al. |
| 2004/0157826 | A1 | 8/2004 | Lampilas et al. |
| 2005/0020572 | A1 | 1/2005 | Aszodi et al. |
| 2006/0019116 | A1 | 1/2006 | Conley et al. |
| 2006/0178357 | A1 | 8/2006 | Buynak et al. |
| 2006/0210883 | A1 | 9/2006 | Chen et al. |
| 2010/0056478 | A1 | 3/2010 | Desarbre et al. |
| 2010/0120715 | A1 | 5/2010 | Burns et al. |
| 2010/0256092 | A1 | 10/2010 | Xia et al. |
| 2011/0288063 | A1 | 11/2011 | Maiti et al. |
| 2012/0040932 | A1 | 2/2012 | Hirst et al. |
| 2013/0316978 | A1 | 11/2013 | Reddy et al. |
| 2013/0345172 | A1 | 12/2013 | Hirst et al. |
| 2014/0194284 | A1 | 7/2014 | Majmudar et al. |
| 2014/0194381 | A1 | 7/2014 | Reddy et al. |
| 2014/0194382 | A1 | 7/2014 | Reddy et al. |
| 2014/0194385 | A1 | 7/2014 | Reddy et al. |
| 2014/0194386 | A1 | 7/2014 | Burns et al. |
| 2014/0206648 | A1 | 7/2014 | Reddy et al. |
| 2015/0119363 | A1 | 4/2015 | Dudley et al. |

FOREIGN PATENT DOCUMENTS

| | | |
|---|---|---|
| JP | 2004291253 A | 10/2004 |
| WO | WO-1987/005297 | 9/1987 |
| WO | WO-1989/010961 | 11/1989 |
| WO | WO-1998/56392 A1 | 12/1998 |
| WO | WO-2000/035904 A1 | 6/2000 |
| WO | WO-2000/035905 A1 | 6/2000 |
| WO | WO-2001/023374 A1 | 4/2001 |
| WO | WO-2001/030149 A1 | 5/2001 |
| WO | WO-2002/022137 A1 | 3/2002 |
| WO | WO-2002/083884 A2 | 10/2002 |
| WO | WO-2003/070714 A1 | 8/2003 |
| WO | WO-2004/039859 A1 | 5/2004 |
| WO | WO-2004/058679 A2 | 7/2004 |
| WO | WO-2004/064755 A2 | 8/2004 |
| WO | WO-2005/033090 A1 | 4/2005 |
| WO | WO-2005/035532 A1 | 4/2005 |
| WO | WO-2005/087700 A2 | 9/2005 |
| WO | WO-2006/091771 A2 | 8/2006 |
| WO | WO-2007/058602 A2 | 5/2007 |
| WO | WO-2007/065288 A2 | 6/2007 |
| WO | WO-2007/095638 A2 | 8/2007 |
| WO | WO-2008/039420 A2 | 4/2008 |
| WO | WO-2008/116813 A1 | 11/2008 |
| WO | WO-2009/046098 A1 | 4/2009 |
| WO | WO-2009/064413 A1 | 5/2009 |
| WO | WO-2009/064414 A1 | 5/2009 |
| WO | WO-2009/091856 A1 | 7/2009 |
| WO | WO-2009/117540 A1 | 9/2009 |
| WO | WO-2009/139834 A1 | 11/2009 |
| WO | WO-2009/140309 A2 | 11/2009 |
| WO | WO-2010/056827 A1 | 5/2010 |
| WO | WO-2010/075286 A1 | 7/2010 |
| WO | WO-2010/097675 A1 | 9/2010 |
| WO | WO-2010/130708 A1 | 11/2010 |
| WO | WO-2010/144338 A1 | 12/2010 |
| WO | WO-2011/017125 A1 | 2/2011 |
| WO | WO-2011/103686 A1 | 9/2011 |
| WO | WO-2012/021455 A1 | 2/2012 |
| WO | WO-2012/067664 A1 | 5/2012 |
| WO | WO-2012/106995 A1 | 8/2012 |
| WO | WO-2013/033461 A1 | 3/2013 |
| WO | WO-2013/053372 A1 | 4/2013 |
| WO | WO-2013/056163 A1 | 4/2013 |
| WO | WO-2013/092979 A1 | 6/2013 |
| WO | WO-2013/122888 A2 | 8/2013 |
| WO | WO-2014/089365 A1 | 6/2014 |
| WO | WO-2014/151958 A1 | 9/2014 |

OTHER PUBLICATIONS

Chemicalland21.com. "Meglumine", Jun. 7, 2011. Downloaded from </www.chemicalland21.com/lifescience/phar/N-METHYL-D-GLUCAMINE.htm>.

Danziger et al., "Automated Site-directed Drug Design: A General Algorithm for Knowledge Acquisition about Hydrogen-bonding Regions at Protein Surfaces", Proc. Royal Soc London, Series B, Biol. Sciences (1989) 236(1283):101-113.

Abdel-Magid et al., "Reductive Amination of Aldehydes and Ketones with Sodium Triacetoxyborohydride: Studies on Direct and Indirect Reductive Amination Procedures", J Org Chem. (1996) 61(11):3849-3862.

Adediran et al., "A 'cephalosporin-like' cyclic depsipeptide: Synthesis and reaction with beta-lactam-recognizing enzymes", Bioorg Med Chem Lett. (1999) 9(3):341-346.

Aizpurua et al., "Synthesis of benzyl halides from aldehydes promoted by halosilanes and 1,1,3,3-tetramethyldisiloxane (TMDS)", Tetrahedron Lett. (1984) 25(10):1103-1104.

Akiyama et al., "N-Hydroxy Amides. Part 6. Synthesis and Spectroscopic Properties of 1-Hydroxypiperazine-2,5-diones", J Chem Soc., Perkin Trans I, (1989) 2:235-239.

Babic et al., "What's new in antibiotic resistance? Focus on beta-lactamases", Drug Res Updates (2006) 9:142-156.

Bassetti et al., "New antibiotics for bad bugs: where are we?", Ann Clin Microbiol Antimicrob. (2013) 12:22-36.

Becker, Daniel E., "Antimicrobial Drugs", Anesth Prog (2013) 60:111-123.

Beenen et al., "Asymmetric copper-catalyzed synthesis of alpha-amino boronate esters from N-tert-butanesulfinyl aldimines", J Am Chem Soc. (2008) 130(22):6910-6911.

Brabez et al., "Design, synthesis, and biological studies of efficient multivalent melanotropin ligands: tools toward melanoma diagnosis and treatment", J Med Chem. (2011) 54(20):7375-7384.

Bush et al., "Minireview: Updated Functional Classification of beta-Lactamases," Antimicrob Agents Chemo. (2010) 54(3):969-976.

Cheng et al., "Synthesis of Aryl Thioethers through the N-Chlorosuccinimide-Promoted Cross-Coupling Reaction of Thiols with Grignard Reagents", J Org Chem. (2012) 77(22):10369-10374.

Coppa et al., "A Facile, Convenient and Selective Homolytic Carbamoylation of Heteroaromatic Bases", Heterocycles (1993) 36(12):2687-2696.

Coutts et al., "Two Efficient Methods for the Cleavage of Pinanediol Boronate Esters Yielding the Free Boronic Acids", Tetrahedron Lett. (1994) 35(29):5109-5112.

Darses et al., "Potassium Organotrifluoroborates: New Perspectives in organic Synthesis", Chem Rev. (2008) 108:288-325.

Davoli et al., "Enantioselective total synthesis of (−)-microcarpalide", Tetrahedron (2005) 61:4427-4436.

Di Gioia et al., "Optically Pure N-Hydroxy-O-triisopropylsilyl-alpha-L-amino Acid Methyl Esters from AlCl3-Assisted Ring Opening of Chiral Oxaziridines by Nitrogen Containing Nucleophiles", J Org Chem. (2005) 70(25):10494-10501.

Eidam et al., "Design, synthesis, crystal structures and antimicrobial activity of sulfonamide boronic acids as beta-lactamase inhibitors", J Med Chem. (2010) 53(21):7852-7863.

(56) References Cited

OTHER PUBLICATIONS

Eissenstat et al., "Aminoalkylindoles: Structure-Activity Relationships of Novel Cannabinoid Mimetics", J Med Chem. (1995) 38(16):3094-3105.

El Nezhawy et al., "Synthesis and antioxidant activity of some thiazolidin-4-one derivatives", Springer; Chemical Monthly/ Monatshefte für Chemie (2009) 140(5):531-539.

Endo et al., "Chemoselective Suzuki coupling of diborylmethane for facile synthesis of benzylboronates", Org Lett. (2011) 13(13):3368-3371.

Giroux, A. "Synthesis of benzylic boronates via palladium-catalyzed cross-coupling reaction of bis(pinacolato)diboron with benzylic halides", Tetrahedron Lett. (2003) 44:233-235.

Hama et al., "Palladium-Catalyzed alpha-Arylation of Zinc Enolates of Esters: Reaction Conditions and Substrate Scope", J Org Chem. (2013) 78(17):8250-8266.

Imanishi et al., "Discovery of a Novel Series of Biphenyl Benzoic Acid Derivatives as Potent and Selective Human beta3-Adrenergic Receptor Agonists with Good Oral Bioavailability. Part I", J Med Chem. (2008) 51(6):1925-1944.

Inglis et al., "Observations on the Deprotection of Pinanediol and Pinacol Boronate Esters via Fluorinated Intermediates", J Org Chem. (2010) 75(2):468-471.

Jagannathan et al., "Synthesis of Boronic Acid Analogues of alpha-Amino Acids by Introducing Side Chains as Electrophiles", J Org Chem. (2001) 66(19):6375-6380.

Jiang et al., "A Practical Synthesis of Cefcapene Pivoxil", Synthesis (2012) 44:207-214.

Kanai et al., "Synthesis of ortho-Acylbenzylboronates via Cross-Coupling Reaction of (Dialkoxyboryl)methylzinc Reagents with Haloarenes. A Stable ortho-Quinodimethane Precursor", (1993) 22(5):845-848.

Kint et al., "New-found fundamentals of bacterial persistence", Trends Microbiol. (2012) 20(12):577-585.

Kose et al., "Synthesis of photochromic 2,3-bis(5-methyl-2-phenyl-4-thiazolyl)-1,4-naphthoquinone derivatives", J Photochem Photobiol. A: Chemistry. (2011) 219(1):58-61.

Kusakabe et al., "Preparation of Optically Acitve 2-Furylcarbinols by Kinetic Resolution Using the Sharpless Reagent and Their Application in Organic Synthesis", J org Chem (1989) 54(9):2085-2091.

Laitar et al., "Catalytic diboration of aldehydes via insertion into the copper-boron bond", J Am Chem Soc. (2006) 128(34):11036-11037.

Li et al., "Stereoselective total synthesis of etnangien and etnangien methyl ester", J Org Chem. (2010) 75(8):2429-2444.

Liang et al., "The Efficient Copper(I) (Hexabenzyl)tren Catalyst and Dendritic Analogues for Green "Click" Reactions between Azides and Alkynes in Organic Solvent and in Water: Positive Dendritic Effects and Monometallic Mechanism", Advance Syn Catal. (2011) 353(18): 3434-3450.

Liu et al., "Selective Protein tyrosine phosphatase 1B inhibitors: Targeting the second phosphotyrosine binding site with non-carboxylic acid-containing ligands", J Med Chem. (2003) 46(16):3437-3440.

Liu et al., "Application of Stereoselective Ether Transfer to the Synthesis of Isotactic Polyethers", J Org Chem. (2010) 75(12):3953-3957.

Matteson et al., "Iodomethaneboronic Esters and Aminomethaneboronic Esters", J Organomet. Chem. (1979) 170:259-264.

Matteson et al., "A Directed Chiral Synthesis of Amino Acids from Boronic Esters", Tetrahedron Lett. (1987) 28(39):4499-4502.

Matteson, D.S., "Asymmetric Synthesis with Boronic Esters", Acc Chem Res. (1988) 21(8):294-300.

Matteson et al., "(Alkoxyalkyl)boronic Ester Intermediates for Asymmetric Synthesis", Organometallics (1996) 15:152-163.

Matteson, "Alpha-Halo Boronic Esters in Asymmetric Synthesis", Tetrahedron (1998) 54(36):10555-10607.

Matteson et al., "Synthesis of a (Beta-acetamido-alpha-acetoxyethyl) boronic ester via azido boronic esters", J Organomet Chem. (2008) 693:2258-2262.

Micalizio et al., "A Boronic Ester Annulation Strategy for Diversity-Oriented Organic Synthesis", Angew Chem Int Ed Engl. (2002) 41(1):152-154.

Montalbetti et al., "Amide bond formation and peptide coupling", Tetrahedron (2005) 61:10827-10852.

Nema et al., "Excipients and Their Role in Approved Injectable Products: Current Usage and Future Directions", PDA J Pharm Sci Technol. (2011) 65(3):287-332.

Ness et al., "Structure-based design guides the improved efficacy of deacylation transition state analogue inhibitors of TEM-1 beta-Lactamase", Biochemistry (2000) 39(18):5312-5321.

Nordmann et al., How to Detect NDM-1 Producers, J. Clin. Micro. (2011) 49:718-721.

Paterson et al., "Extended-Spectrum beta-Lactamases: a Clinical Update", Clin Microbiol Rev. (2005) 18(4):657-686.

Pintaric et al., "An Opportunity for Mg-Catalyzed Grignard-Type Reactions: Direct Coupling of Benzylic Halides with Pinacolborane with 10 mol % of Magnesium", J Am Chem Soc. (2010) 132(34): 11825-11827.

Powell et al., "Compendium of excipients for parenteral formulations", PDA J Pharm Sci Technol. (1998) 52(5):238-311.

Robak et al., "Synthesis and applications of tert-butanesulfinamide", Chem Rev. (2010) 110(6):3600-3740.

Selander et al., "Palladium-catalyzed allylic C—OH functionalization for efficient synthesis of functionalized allylsilanes", J Am Chem Soc. (2011) 133(3):409-411.

Shaffer, Robyn Kroop, "The Challenge of Antibiotic-Resistant *Staphylococcus*: Lessons from Hospital Nurseries in the mid-20th Century", Yale J Biol Med. (2013) 86:261-270.

Shao et al., "Asymmetric hydrogenation of 3,5-Dioxoesters catalyzed by Ru-binap complex: A short step asymmetric synthesis of 6-substituted 5,6-dehydro-2-pyrones", Tetrahedron (1993) 49(10):1997-2010.

Singh et al., "Asymmetric Homologation of Boronic Esters Bearing Azido and Silyloxy Substituents", J Org Chem. (2000) 65(20):6650-6653 and Erratum: J Org Chem. (2001) 66(22):7560.

Sliwka et al., "Synthetic Sulfur Carotenoids II: Optically Active Carotenoid Thiols", Tetrahedron: Asymmetry (1993) 4(3):361-368.

Solladié et al., "First Stereocontrolled Synthesis of the (3S,5R,7R,10R,11R)-C1-C13 Fragment of Nystatin A(1)", J Org Chem. (1999) 64(15):5447-5452.

Teo et al., "Efficient and highly aldehyde selective Wacker oxidation", Org Lett. (2012) 14(13):3237-3239.

Theuretzbacher et al., "Update on antibacterial and antifungal drugs—can we master the resistance crisis?", Curr Opin Pharmacol. (2011) 11:429-432.

Vitor et al., "Rhenium(I)- and technetium(I) tricarbonyl complexes anchored by bifunctional pyrazole-diamine and pyrazole-dithioether chelators", J Organometal Chem (2004) 689(25):4764-4774.

Waley, Stephen G., "A quick method for the determination of inhibition constants", Biochem J. (1982) 205(3):631-633.

Walsh et al., "Metallo-beta-Lactamases: the Quiet before the Storm?", Clin Microbiol Rev. (2005) 18(2):306-325.

Yanagisawa et al., "Nonpeptide angiotensin II receptor antagonists: synthesis, biological activities, and structure-activity relationships of imidazole-5-carboxylic acids bearing alkyl, alkenyl, and hydroxyalkyl substituents at the 4-position and their related compounds", J Med Chem. (1996) 39(1):323-338.

Yuen et al., "Deprotection of pinacolyl boronate esters via hydrolysis of intermediate potassium trifluoroborates", Tetrahedron Lett. (2005)46(46):7899-7903.

International Search Report and Written Opinion dated Mar. 12, 2014 for International Patent Application No. PCT/US2014/010106, filed Jan. 2, 2014.

International Search Report and Written Opinion dated Mar. 12, 2014 for International Patent Application No. PCT/US2014/010107, filed Jan. 2, 2014.

U.S. Office Action, dated Apr. 1, 2014, in U.S. Appl. No. 13/898,959.

(56) References Cited

OTHER PUBLICATIONS

Allen et al., "Ansel's Pharmaceutical Dosage Forms and Drug Delivery Systems", 8th Edition (2004).
Arya et al., "Advances in asymmetric enolate methodology", Tetrahedron (2000) 56:917-947.
Biedrzycki et al., "Derivatives of Tetrahedral Boronic Acids", Journal of Organometallic Chemistry, (1992) 431:255-270.
Bou et al., "Cloning, Nucleotide Sequencing, and Analysis of the Gene Encoding an AmpC Beta-Lactamase in Acinetobacter baumannii", Antimicrobial Agents and Chemotherapy, (2000), 44(2):428-432.
Bou et al., "OXA-24, a Novel Class D beta-Lactamase with Carbapenemase Activity in an Acinetobacter baumannii Clinical Strain", Antimicrobial Agents and Chemotherapy, (2000) 44(6):1556-1561, Erratum (2006) 50(6) 2280.
Brosz et al., "Resolution of alpha-aminoboronic esters by diastereoselective crystallization with pinanediols. Confirmation by x-ray analysis", Tetrahedron: Asymmetry (1997) 8(9):1435-1440.
Clinical and Laboratory Standards Institute (formerly NCCLS, National Committee for Clinical Laboratory Standards), "Methods for Dilution Antimicrobial Susceptibility Tests for Bacteria That Grow Aerobically", CLSI (Jan. 2006) M7-A7 26(2).
Clinical and Laboratory Standards Institute (formerly NCCLS, National Committee for Clinical Laboratory Standards), "Methods for Dilution Antimicrobial Susceptibility Tests for Bacteria That Grow Aerobically", CLSI (Jan. 2009) M07-A8 29(2).
Fan, et al. (2009): STN International HCAPLUS database, Columbus (OH), accession No. 2009: 425839.
Farquhar et al., "Intensely potent doxorubicin analogues: structure-activity relationship", J. Med. Chem. (1998) 41(6):965-972.
Ghosh, et al., "Enantioselective Total Synthesis of (+)-Largazole, a Potent Inhibitor of Histone Deacetylase", Organic Letters (2008) 10(17):3907-3909.
Gossinger et al., "Towards EPC-syntheses of the structural class of cochleamycins and macquarimicins. Part 3: EPC-syntheses of the beta-keto lactone subunits and first attempts towards the syntheses of the pentacyclic antibiotics of this group", Tetrahedron (2007) 63:8336-8350.
International Search Report and Written Opinion in PCT Application No. PCT/US2011/046957, filed Aug. 8, 2011, dated Sep. 14, 2011.
International Search Report and Written Opinion in PCT Application No. PCT/US2012/053233 filed Aug. 30, 2012, dated Nov. 5, 2012.
International Search Report and Written Opinion in PCT Application No. PCT/US2013/025621 filed Feb. 11, 2013, dated May 9, 2013.
International Search Report and Written Opinion in PCT Application No. PCT/US2013/044377 filed Jun. 5, 2013, dated Aug. 29, 2013.
Ishii, et al, "In Vitro Potentiation of Carbapenems with ME1071, a Novel Metallo-Beta-Lactamase Inhibitor, against Metallo-Beta-Lactamase Producing Pseudomonas aeruginosa Clinical Isolates", Antimicrobial Agents and Chemotherapy doi:10.1128/AAC.01397-09 (2010) 54(9):3625-3629.
Ito, et al., "An efficient constructive method for a tricyclic system: an important intermediate for the synthesis of tricycloclavulone", Tetrahedron Letters (2003) 44:1259-1261.
Jadhav, et al., "Direct Synthesis of [alpha-[(tert-Butoxycarbonyl)amino]alkyl]-boronates from (alpha-Haloalkyl)boronates", J. Org Chem. (1996) 61(22):7951-7954.
Kotha et al., "Recent applications of the suzuki-miyaura cross-coupling reaction in organic synthesis", Tetrahedron (2002) 58:9633-9695.

Kumar et al., "Synthesis of intermediates for the lactone moiety of mevinic acids via tellurium chemistry", J. Org. Chem., (1994) 59(17):4760-4764.
Li, et al, "Novel macrocyclic HCV NS3 protease inhibitors derived from α-amino cyclic boronates", Bioorganic & Medicinal Chemistry Letters (2010) 20:5695-5700.
Li, et al., "Synthesis and evaluation of novel alpha-amino cyclic boronates as inhibitors of HCV NS3 protease", Bioorganic & Medicinal Chemistry Letters (2010) 20:3550-3556.
Livermore, et al., "Activities of NXL 104 Combinations with Ceftazidime and Aztreonam against Carbapenemase-Producing Enterobacteriaceae", Antimicrobial Agents and Chemotherapy (Jan. 2011) 55(1):390-394.
Matteson, "Boronic esters in stereodirected synthesis", Tetrahedron (1989) 45(7):1859-1885.
Matteson et al., "A stereospecific convergent coupling of nucleophilic and electrophilic chiral carbons", J. Am. Chem. Soc. (1989) 111:4399-4402.
Matteson et al., "Synthesis of asymmetrically deuterated glycerol and dibenzylglyceraldehyde via boronic esters", J. Am. Chem. Soc. (1990) 112:3964-3969.
Meanwell, "Synopsis of Some Recent Tactical Application of Bioisosteres in Drug Design", Journal of Medicinal Chemistry (2011) 54:2529-2591.
Montefour, et al., "Acinetobacter baumannii: An Emerging Multidrug-Resistant Pathogen in Critical Care", Critical Care Nurse (2008) 28(1):15-25; quiz 26.
Morandi, et al., "Structure-based optimization of cephalothin-analogue boronic acids as beta-lactamase inhibitors", Bioorganic & Medicinal Chemistry (2008) 16(3):1195-1205; Epub Nov. 7, 2007.
Panek et al., "Diastereoselectivity in the borane methyl sulfide promoted hydroboration of .alpha.-alkoxy-.beta, gamma.-unsaturated esters. Documentation of an alkoxy-directed hydroboration reaction", J. Org. Chem. (1992) 57(20):5288-5290.
Perez, et al., "Why are we afraid of Acinetobacter baumannii?", Expert Rev. Anti Infect. Ther. (2008) 6(3):269-271.
Reissig et al.,"High diastereoselection in the alkylation of siloxy-substituted methyl cyclopropanecarboxylates: consequence of a pyramidal ester enolate anion?", J. Am. Chem. Soc. (1982) 104:1735-1737.
Rodriguez-Martinez, et al., "VIM-19, a Metallo-Beta-Lactamase with Increased Carbapenemase Activity from Escherichia coli and Klebsiella pneumonia", Antimicrobial Agents and Chemotherapy (2010) 54(1):471-476.
Sawyer, et al., "Physical Properties and Synthetic Utility of α-Alkoxyorganolithium Species as Studied through Ligand Selectivity in Tin-Lithium Exchange", J. Am. Chem. Soc. (1988) 110(3):842-853.
Souto et al., "Synthesis and biological characterization of the histone deacetylase inhibitor largazole and c7-modified analogues", J. Med. Chem. (2010) 53(12):4654-4667.
Spiegel et al., "CP-263, 114 synthetic studies. Construction of an isotwistane ring system via rhodium carbenoid C—H insertion", Tetrahedron (2002) 58:6545-6554.
U.S. Office Action, dated Aug. 20, 2013, in U.S. Appl. No. 13/205,112.
Vasil'Ev, et al., (1977): STN International HCAPLUS database, Columbus (OH), accession No. 1977: 72730.
Wang et al., "Recognition and resistance in TEM beta-lactamase", Biochemistry (2003) 42(28):8434-8444.
Wohlrab et al., "Total synthesis of plusbacin A3: a depsipeptide antibiotic active against vancomycin-resistant bacteria", J. Am. Chem. Soc. (2007) 129:4175-4177.
Xia et al., "Synthesis and SAR of novel benzoxaborales as a new class of beta-lactamase inhibitors", Bioorganic & Medicinal Chemistry Letters (2011) 21(8): 2533-2536.
Yamamoto et al., "Iridium-catalyzed hydroboration of alkenes with pinacolborane", Tetrahedron (2004) 60:10695-10700.

* cited by examiner

CYCLIC BORONIC ACID ESTER DERIVATIVES AND THERAPEUTIC USES THEREOF

INCORPORATION BY REFERENCE TO ANY PRIORITY APPLICATIONS

This application is a continuation of U.S. patent application Ser. No. 13/843,579, filed Mar. 15, 2013, which claims the benefit of priority to U.S. Provisional Patent Application Ser. No. 61/656,452, filed Jun. 6, 2012, each of which is incorporated by reference in its entirety. Any and all applications for which a foreign or domestic priority claim is identified in the Application Data Sheet as filed with the present application, or any correction thereto, are hereby incorporated by reference under 37 CFR 1.57.

FIELD

The present invention relates to antimicrobial compounds, compositions, their use and preparation as therapeutic agents. In particular, the present invention relates to use of cyclic boronic acid ester compounds in combination with carbapenems.

BACKGROUND

Antibiotics have been effective tools in the treatment of infectious diseases during the last half-century. From the development of antibiotic therapy to the late 1980s there was almost complete control over bacterial infections in developed countries. However, in response to the pressure of antibiotic usage, multiple resistance mechanisms have become widespread and are threatening the clinical utility of anti-bacterial therapy. The increase in antibiotic resistant strains has been particularly common in major hospitals and care centers. The consequences of the increase in resistant strains include higher morbidity and mortality, longer patient hospitalization, and an increase in treatment costs.

Various bacteria have evolved β-lactam deactivating enzymes, namely, β-lactamases, that counter the efficacy of the various β-lactams. β-lactamases can be grouped into 4 classes based on their amino acid sequences, namely, Ambler classes A, B, C, and D. Enzymes in classes A, C, and D include active-site serine β-lactamases, and class B enzymes, which are encountered less frequently, are Zn-dependent. These enzymes catalyze the chemical degradation of β-lactam antibiotics, rendering them inactive. Some β-lactamases can be transferred within and between various bacterial strains and species. The rapid spread of bacterial resistance and the evolution of multi-resistant strains severely limits β-lactam treatment options available.

The increase of class D β-lactamase-expressing bacterium strains such as Acinetobacter baumannii has become an emerging multidrug-resistant threat. A. baumannii strains express A, C, and D class β-lactamases. The class D β-lactamases such as the OXA families are particularly effective at destroying carbapenem type β-lactam antibiotics, e.g., imipenem, the active carbapenems component of Merck's Primaxin® (Montefour, K.; et al. Crit. Care Nurse 2008, 28, 15; Perez, F. et al. Expert Rev. Anti Infect. Ther. 2008, 6, 269; Bou, G.; Martinez-Beltran, J. Antimicrob. Agents Chemother. 2000, 40, 428. 2006, 50, 2280; Bou, G. et al, J. Antimicrob. Agents Chemother. 2000, 44, 1556). This has imposed a pressing threat to the effective use of drugs in that category to treat and prevent bacterial infections. Indeed the number of catalogued serine-based β-lactamases has exploded from less than ten in the 1970s to over 300 variants. These issues fostered the development of five "generations" of cephalosporins. When initially released into clinical practice, extended-spectrum cephalosporins resisted hydrolysis by the prevalent class A β-lactamases, TEM-1 and SHV-1. However, the development of resistant strains by the evolution of single amino acid substitutions in TEM-1 and SHV-1 resulted in the emergence of the extended-spectrum β-lactamase (ESBL) phenotype.

New β-lactamases have recently evolved that hydrolyze the carbapenem class of antimicrobials, including imipenem, biapenem, doripenem, meropenem, and ertapenem, as well as other β-lactam antibiotics. These carbapenemases belong to molecular classes A, B, and D. Class A carbapenemases of the KPC-type predominantly in Klebsiella pneumoniae but now also reported in other Enterobacteriaceae, Pseudomonas aeruginosa and Acinetobacter baumannii. The KPC carbapenemase was first described in 1996 in North Carolina, but since then has disseminated widely in the US. It has been particularly problematic in the New York City area, where several reports of spread within major hospitals and patient morbidity have been reported. These enzymes have also been recently reported in France, Greece, Sweden, United Kingdom, and an outbreak in Germany has recently been reported. Treatment of resistant strains with carbapenems can be associated with poor outcomes.

Another mechanism of β-lactamase mediated resistance to carbapenems involves combination of permeability or efflux mechanisms combined with hyper production of beta-lactamases. One example is the loss of a porin combined in hyperproduction of ampC beta-lactamase results in resistance to imipenem in Pseudomonas aeruginosa. Efflux pump over expression combined with hyperproduction of the ampC β-lactamase can also result in resistance to a carbapenem such as meropenem.

Because there are three major molecular classes of serine-based β-lactamases, and each of these classes contains significant numbers of β-lactamase variants, inhibition of one or a small number of β-lactamases is unlikely to be of therapeutic value. Legacy β-lactamase inhibitors are largely ineffective against at least Class A carbapenemases, against the chromosomal and plasmid-mediated Class C cephalosporinases and against many of the Class D oxacillinases. Therefore, there is a need for improved β-lactamase inhibitors.

SUMMARY

Some embodiments described herein relate to a method for treating a bacterial infection, comprising administering to a subject in need thereof a composition comprising a cyclic boronic acid ester compound I or a pharmaceutically acceptable salt thereof and a carbapenem antibacterial agent to achieve an in vivo Compound I plasma concentration $C_{max}$ from about 1 mg/L to about 500 mg/L.

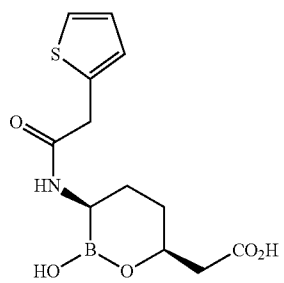

(Compound I)

Some embodiments described herein relate to a method for treating a bacterial infection, comprising administering to a subject in need thereof a composition comprising a cyclic boronic acid ester compound I or a pharmaceutically acceptable salt thereof and a carbapenem antibacterial agent to achieve an in vivo Compound I 24 h AUC from about 3 mg*h/L to about 800 mg*h/L.

In some embodiments, the carbapenem antibacterial agent is selected from the group consisting of Imipenem, Biapenem, Doripenem, Meropenem, and Ertapenem. In some such embodiments, the carbapenem antibacterial agent is Biapenem.

In some embodiments, Compound I is administered in a dosage range from about 0.1 mg/kg to about 1000 mg/kg of body weight. In some further embodiments, Compound I is administered in a dosage range from about 0.5 mg/kg to about 150 mg/kg of body weight.

In some embodiments, the composition is administered intravenously.

In some embodiments, the infection is caused by a bacteria selected from *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, or *Bacteroides splanchnicus*.

In some embodiments, the composition further comprises an additional medicament selected from an antibacterial agent, antifungal agent, an antiviral agent, an anti-inflammatory agent, or an anti-allergic agent.

In some embodiments, the subject treated by the method described above is a mammal. In some further embodiments, the subject is a human.

DETAILED DESCRIPTION

Definitions

Figure 1:
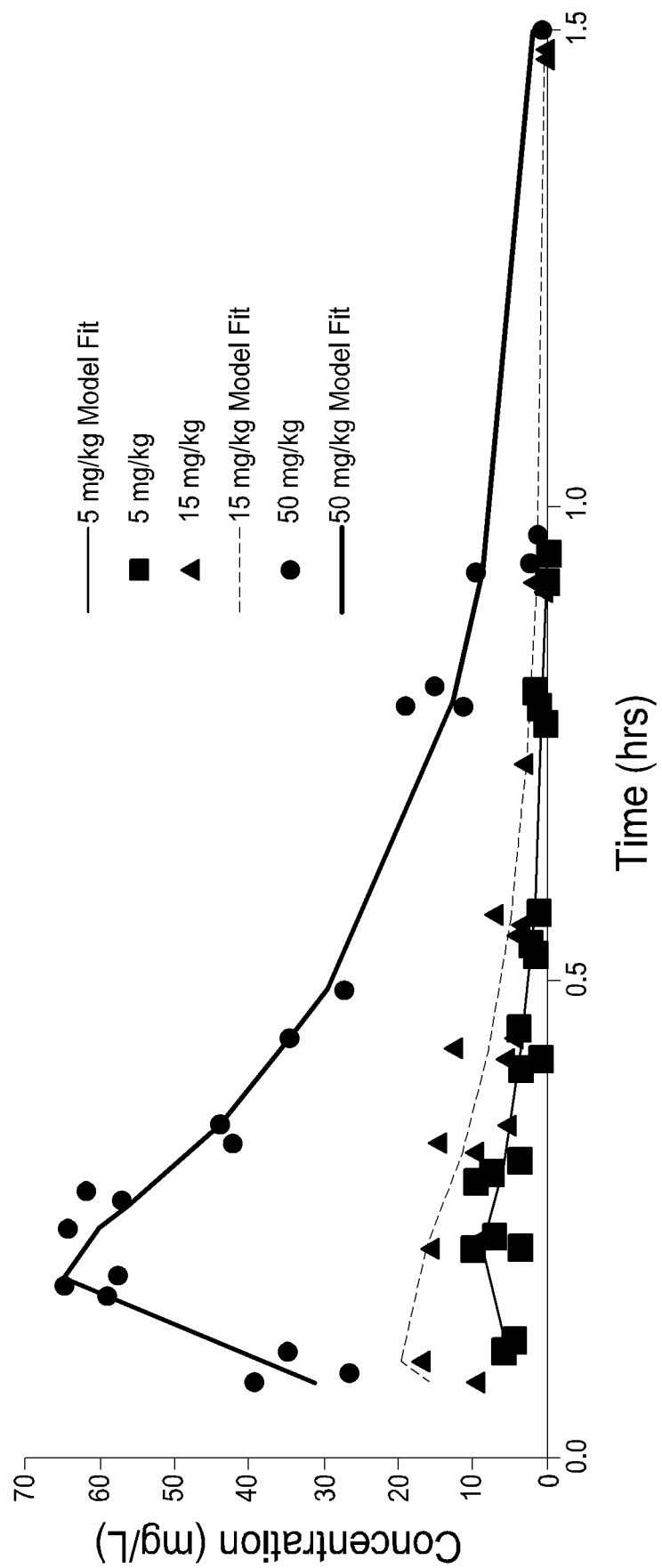
FIG. 1 is a graph depicting the plasma concentration profile of 5, 15 or 50 mg/kg Compound I as a function of time after administration to Swiss Webster mice.

The compounds provided herein may encompass various stereochemical forms. The compounds also encompasses diastereomers as well as optical isomers, e.g. mixtures of enantiomers including racemic mixtures, as well as individual enantiomers and diastereomers, which arise as a consequence of structural asymmetry in certain compounds. Separation of the individual isomers or selective synthesis of the individual isomers is accomplished by application of various methods which are well known to practitioners in the art.

The term "agent" or "test agent" includes any substance, molecule, element, compound, entity, or a combination thereof. It includes, but is not limited to, e.g., protein, polypeptide, peptide or mimetic, small organic molecule, polysaccharide, polynucleotide, and the like. It can be a natural product, a synthetic compound, or a chemical compound, or a combination of two or more substances. Unless otherwise specified, the terms "agent", "substance", and "compound" are used interchangeably herein.

The term "mammal" is used in its usual biological sense. Thus, it specifically includes humans, cattle, horses, dogs, cats, rats and mice but also includes many other species.

The term "microbial infection" refers to the invasion of the host organism, whether the organism is a vertebrate, invertebrate, fish, plant, bird, or mammal, by pathogenic microbes. This includes the excessive growth of microbes that are normally present in or on the body of a mammal or other organism. More generally, a microbial infection can be any situation in which the presence of a microbial population(s) is damaging to a host mammal. Thus, a mammal is "suffering" from a microbial infection when excessive numbers of a microbial population are present in or on a mammal's body, or when the effects of the presence of a microbial population(s) is damaging the cells or other tissue of a mammal. Specifically, this description applies to a bacterial infection. Note that the compounds of preferred embodiments are also useful in treating microbial growth or contamination of cell cultures or other media, or inanimate surfaces or objects, and nothing herein should limit the preferred embodiments only to treatment of higher organisms, except when explicitly so specified in the claims.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions. In addition, various adjuvants such as are commonly used in the art may be included. These and other such compounds are described in the literature, e.g., in the Merck Index, Merck & Company, Rahway, N.J. Considerations for the inclusion of various components in pharmaceutical compositions are described, e.g., in Gilman et al. (Eds.) (1990); Goodman and Gilman's: The Pharmacological Basis of Therapeutics, 8th Ed., Pergamon Press.

The term "pharmaceutically acceptable salt" refers to salts that retain the biological effectiveness and properties of the compounds of the preferred embodiments and, which are not biologically or otherwise undesirable. In many cases, the compounds of the preferred embodiments are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

"Solvate" refers to the compound formed by the interaction of a solvent and an EPI, a metabolite, or salt thereof. Suitable solvates are pharmaceutically acceptable solvates including hydrates.

"Subject" as used herein, means a human or a non-human mammal, e.g., a dog, a cat, a mouse, a rat, a cow, a sheep, a pig, a goat, a non-human primate or a bird, e.g., a chicken, as well as any other vertebrate or invertebrate.

A therapeutic effect relieves, to some extent, one or more of the symptoms of the infection, and includes curing an infection. "Curing" means that the symptoms of active infection are eliminated, including the elimination of excessive members of viable microbe of those involved in the infection. However, certain long-term or permanent effects of the infection may exist even after a cure is obtained (such as extensive tissue damage).

"Treat," "treatment," or "treating," as used herein refers to administering a pharmaceutical composition for prophylactic and/or therapeutic purposes. The term "prophylactic treatment" refers to treating a patient who is not yet infected, but who is susceptible to, or otherwise at risk of, a particular infection, whereby the treatment reduces the likelihood that the patient will develop an infection. The term "therapeutic treatment" refers to administering treatment to a patient already suffering from an infection.

Methods of Treatment

Some embodiments described herein relate to a method for treating a bacterial infection, comprising administering to a subject in need thereof a composition comprising compound I or a pharmaceutically acceptable salt thereof and a carbapenem antibacterial agent to achieve an in vivo Compound I plasma concentration $C_{max}$ from about 1 mg/L to about 500 mg/L. In some embodiments, Compound I plasma concentration $C_{max}$ achieved by the methods described herein is from about 3 mg/L to about 400 mg/L. In some embodiments, Compound I plasma concentration $C_{max}$ achieved by the methods described herein is from about 5 mg/L to about 300 mg/L. In some embodiments, Compound I plasma concentration $C_{max}$ achieved by the methods described herein is from about 10 mg/L to about 200 mg/L. In some embodiments, Compound I plasma concentration $C_{max}$ achieved by the methods described herein is from about 10 mg/L to about 50 mg/L.

Some embodiments described herein relate to a method for treating a bacterial infection, comprising administering to a subject in need thereof a composition comprising compound I or a pharmaceutically acceptable salt thereof and a carbapenem antibacterial agent to achieve an in vivo Compound I 24 h AUC from about 3 mg*h/L to about 800 mg*h/L. In some embodiments, Compound I 24 h AUC achieved by the method described herein is from about 10 mg*h/L to about 700 mg*h/L. In some embodiments, Compound I AUC achieved by the method described herein is from about 20 mg*h/L to about 600 mg*h/L. In some embodiments, Compound I 24 h AUC achieved by the method described herein is from about 45 mg*h/L to about 500 mg*h/L.

In some embodiments, the carbapenem antibacterial agent is selected from the group consisting of Imipenem, Biapenem, Doripenem, Meropenem, and Ertapenem. In some such embodiments, the carbapenem antibacterial agent is Biapenem.

In some embodiments, Compound I is administered in a dosage range from about 0.1 mg/kg to about 1000 mg/kg of body weight. In some further embodiments, Compound I is administered in a dosage range from about 0.5 mg/kg to about 500 mg/kg of body weight. In some embodiments, Compound I is administered in a dosage range from about 1 mg/kg to about 300 mg/kg. In some embodiments, Compound I is administered in a dosage range from about 1.5 mg/kg to about 150 mg/kg.

In some embodiments, Compound I plasma clearance achieved by the methods described herein is from about 0.01 L/h/kg to about 5 L/h/kg. In some embodiments, Compound I plasma clearance achieved by the methods described herein is from 0.025 L/hr/kg to about 2.2 L/h/kg. In some embodiments, Compound I plasma clearance achieved by the methods described herein is from about 0.05 L/h/kg to about 1 L/h/kg.

In some embodiments, Compound I half-life achieved by the methods described herein is from about 0.05 hr to about 10 hrs. In some embodiments, Compound I half-life achieved by the methods described herein is from about 0.1 hr to about 7 hrs. In some embodiments, Compound I half-life achieved by the methods described herein is from about 0.3 hr to about 5 hrs.

The above-described pharmacokinetic parameters may be achieved via a variety of methods, including by selection of dose, administration duration (e.g., IV infusion rate), and selection of formulation (e.g., selection of immediate or sustained-release formulations).

In some embodiments, the composition is administered intravenously.

Some embodiments include co-administering Compound I, its enatiomer, diastereomer, tautomer or pharmaceutically acceptable salt thereof, composition, and/or pharmaceutical composition described herein, with a carbapenem antibacterial agent. By "co-administration," it is meant that the two or more agents may be found in the patient's bloodstream at the same time, regardless of when or how they are actually administered. In one embodiment, the agents are administered simultaneously. In one such embodiment, administration in combination is accomplished by combining the agents in a single dosage form. When combining the agents in a single dosage form, they may be physically mixed (e.g., by co-dissolution or dry mixing) or may form an adduct or be covalently linked such that they split into the two or more active ingredients upon administration to the patient. In another embodiment, the agents are administered sequentially. In one embodiment the agents are administered through the same route, such as orally. In another embodiment, the agents are administered through different routes, such as one being administered orally and another being administered i.v.

Further embodiments include administering a combination of Compound I, a carbapenem antibacterial agent, and an additional medicament selected from an antibacterial agent, antifungal agent, an antiviral agent, an anti-inflammatory agent, or an anti-allergic agent to a subject in need thereof.

Some embodiments include co-administration of a combination of Compound I and a carbapenem antibacterial agent with an additional antibacterial agent such as a β-lactam. In some embodiment, the carbapenem antibacterial agent is Biapenem.

Preferred embodiments of additional medicaments include β-lactams such as Ceftazidime, Doripenem, Ertapenem, Imipenem, Meropenem, ME1036, Tomopenem, Razupenem, and Panipenem.

Some embodiments include co-administration of a combination of Compound I and a carbapenem antibacterial agent described herein with an additional agent, wherein the additional agent comprises a monobactam. Examples of monobactams include aztreonam, tigemonam, BAL 30072, SYN 2416 (BAL19764), and carumonam.

Some embodiments include co-administration of a combination of Compound I and a carbapenem antibacterial agent described herein with an additional agent, wherein the additional agent comprises a Class A, B, C, or D beta-lactamase inhibitor. An example of a class B beta lactamase inhibitor includes ME1071 (Yoshikazu Ishii et al, "In Vitro Potentiation of Carbapenems with ME1071, a Novel Metallo-β-Lactamase Inhibitor, against Metallo-β-lactamase Producing *Pseudomonas aeruginosa* Clinical Isolates." Antimicrob. Agents Chemother. doi:10.1128/AAC.01397-09 (July 2010)). Other examples of beta-lactamase inhibitors administered as an additional agent include clavulanic acid, tazobactam, sulbactam, avibactam (NXL-104), MK-7655, BAL29880, SYN-2190, BLI-489, AM-112, and ME1071. MK-7655 has the following structure:

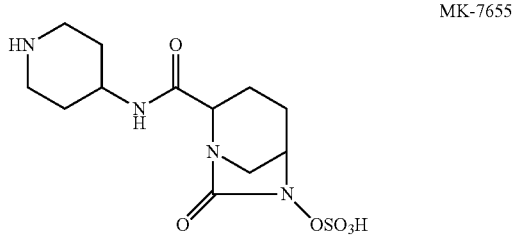

MK-7655

Indications

The compositions comprising Compound I and a carbapenem compound described herein can be used to treat bacterial infections. Bacterial infections that can be treated with a combination of Compound I and a carbapenem antibacterial agent described herein can comprise a wide spectrum of bacteria. Example organisms include gram-positive bacteria, gram-negative bacteria, aerobic and anaerobic bacteria, such as *Staphylococcus, Lactobacillus, Streptococcus, Sarcina, Escherichia, Enterobacter, Klebsiella, Pseudomonas, Acinetobacter, Mycobacterium, Proteus, Campylobacter, Citrobacter, Nisseria, Baccillus, Bacteroides, Peptococcus, Clostridium, Salmonella, Shigella, Serratia, Haemophilus, Brucella* and other organisms.

More examples of bacterial infections include *Pseudomonas aeruginosa, Pseudomonas fluorescens, Pseudomonas acidovorans, Pseudomonas alcaligenes, Pseudomonas putida, Stenotrophomonas maltophilia, Burkholderia cepacia, Aeromonas hydrophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Francisella tularensis, Morganella morganii, Proteus mirabilis, Proteus vulgaris, Providencia alcalifaciens, Providencia rettgeri, Providencia stuartii, Acinetobacter baumannii, Acinetobacter calcoaceticus, Acinetobacter haemolyticus, Yersinia enterocolitica, Yersinia pestis, Yersinia pseudotuberculosis, Yersinia intermedia, Bordetella pertussis, Bordetella parapertussis, Bordetella bronchiseptica, Haemophilus influenzae, Haemophilus parainfluenzae, Haemophilus haemolyticus, Haemophilus parahaemolyticus, Haemophilus ducreyi, Pasteurella multocida, Pasteurella haemolytica, Branhamella catarrhalis, Helicobacter pylori, Campylobacter fetus, Campylobacter jejuni, Campylobacter coli, Borrelia burgdorferi, Vibrio cholerae, Vibrio parahaemolyticus, Legionella pneumophila, Listeria monocytogenes, Neisseria gonorrhoeae, Neisseria meningitidis, Kingella, Moraxella, Gardnerella vaginalis, Bacteroides fragilis, Bacteroides distasonis, Bacteroides* 3452A homology group, *Bacteroides vulgatus, Bacteroides ovalus, Bacteroides thetaiotaomicron, Bacteroides uniformis, Bacteroides eggerthii, Bacteroides splanchnicus, Clostridium difficile, Mycobacterium tuberculosis, Mycobacterium avium, Mycobacterium intracellulare, Mycobacterium leprae, Corynebacterium diphtherias, Corynebacterium ulcerans, Streptococcus pneumoniae, Streptococcus agalactiae, Streptococcus pyogenes, Enterococcus faecalis, Enterococcus faecium, Staphylococcus aureus, Staphylococcus epidermidis, Staphylococcus saprophyticus, Staphylococcus intermedius, Staphylococcus hyicus* subsp. *hyicus, Staphylococcus haemolyticus, Staphylococcus hominis,* or *Staphylococcus saccharolyticus*.

In some embodiments, the infection is caused by a bacteria selected from *Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter* coli, *Vibrio cholerae*, *Vibrio parahaemolyticus*, *Legionella pneumophila*, *Listeria monocytogenes*, *Neisseria gonorrhoeae*, *Neisseria meningitidis*, *Moraxella*, *Bacteroides* *Bacteroides vulgatus*, *Bacteroides ovalus*, *Bacteroides thetaiotaomicron*, *Bacteroides uniformis*, *Bacteroides eggerthii*, or *Bacteroides splanchnicus*.

In some embodiments, the composition further comprises an additional medicament selected from an antibacterial agent, antifungal agent, an antiviral agent, an anti-inflammatory agent, or an anti-allergic agent.

In some embodiments, the subject treated by the method described above is a mammal. In some further embodiments, the subject is a human.

Antibacterial Compounds

Compounds I and II have the structures shown as follows:

Compound I

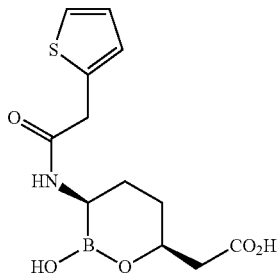

Compound II

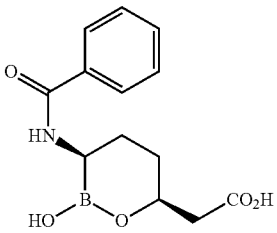

In some embodiments, due to the facile exchange of boron esters, the compounds described herein may convert to or exist in equilibrium with alternate forms. Accordingly, in some embodiments, Compound I may exist in combination with one or more of these forms. For example, Compound I may exist in combination with one or more open-chain form (Formula Ia), dimeric form (Formula Ib), cyclic dimeric form (Formula Ic), trimeric form (Formula Id), cyclic trimeric form (Formula Ie), and the like.

Ia

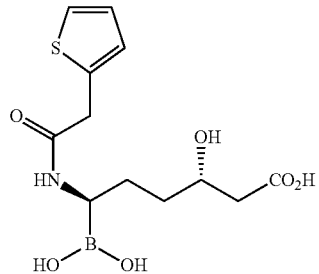

Ib

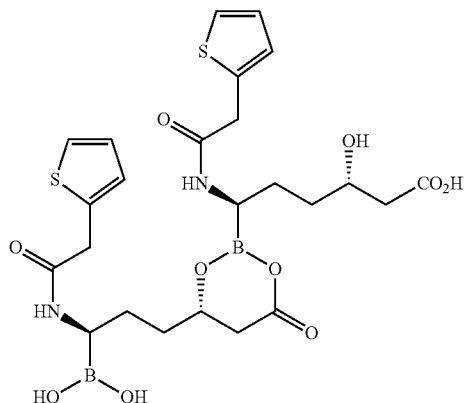

Ic

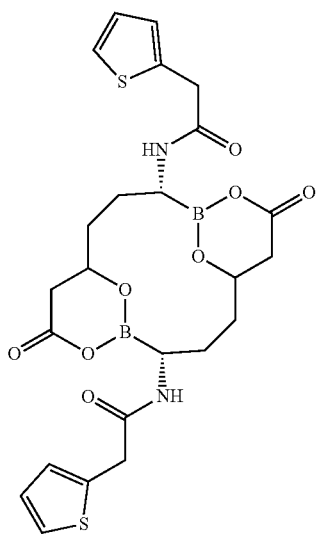

Id

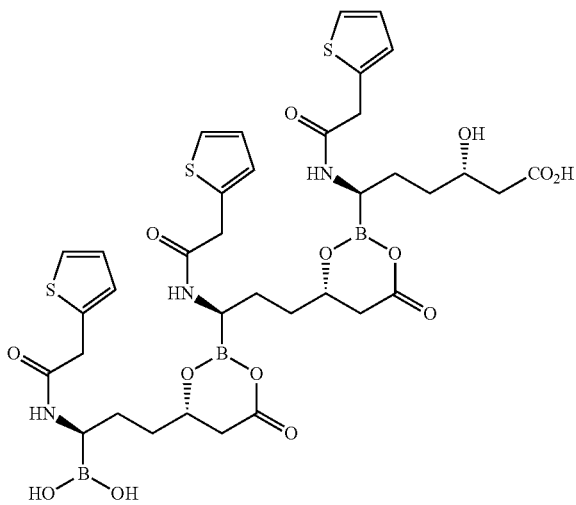

Ie

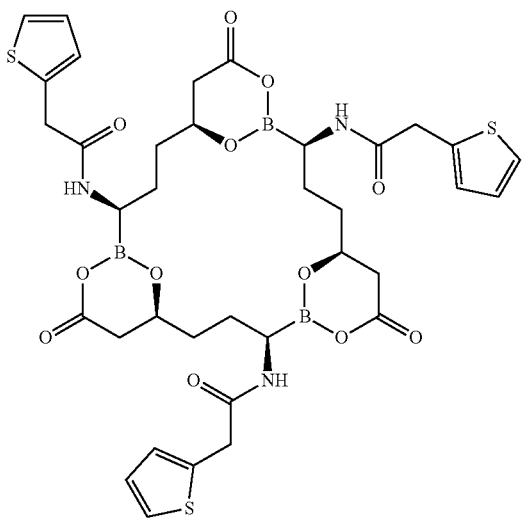

Some embodiments include methods for treating or preventing a bacterial infection comprising administering to a subject in need thereof, an effective amount of Compound I and a carbapenem antibacterial agent, wherein Compound I can be in any one of the forms described above or a combination thereof. In some embodiments, the carbapenem antibacterial agent is selected from the group consisting of Imipenem, Biapenem, Doripenem, Meropenem, and Ertapenem. In one embodiment, the carbapenem is Biapenem.

Some embodiments include the use of Compound I in combination with a carbapenem antibacterial agent in the preparation of a medicament for the treatment or prevention of a bacterial infection, wherein Compound I can be in any one of the forms described above or a combination thereof. In some embodiments, the carbapenem antibacterial agent is selected from the group consisting of Imipenem, Biapenem, Doripenem, Meropenem, and Ertapenem. In one embodiment, the carbapenem is Biapenem.

Some embodiments further comprise administering an additional medicament, either is a separate composition or in the same composition.

In some embodiments, the additional medicament includes an antibacterial agent, antifungal agent, an antiviral agent, an anti-inflammatory agent or an anti-allergic agent.

In some embodiments, the additional medicament comprises an antibacterial agent such as a β-lactam.

In some embodiments, the β-lactam includes Amoxicillin, Ampicillin (Pivampicillin, Hetacillin, Bacampicillin, Metampicillin, Talampicillin), Epicillin, Carbenicillin (Carindacillin), Ticarcillin, Temocillin, Azlocillin, Piperacillin, Mezlocillin, Mecillinam (Pivmecillinam), Sulbenicillin, Benzylpenicillin (G), Clometocillin, Benzathine benzylpenicillin, Procaine benzylpenicillin, Azidocillin, Penamecillin, Phenoxymethylpenicillin (V), Propicillin, Benzathine phenoxymethylpenicillin, Pheneticillin, Cloxacillin (Dicloxacillin, Flucloxacillin), Oxacillin, Meticillin, Nafcillin, Faropenem, Biapenem, Doripenem, Ertapenem, Imipenem, Meropenem, Panipenem, Tomopenem, Razupenem, Cefazolin, Cefacetrile, Cefadroxil, Cefalexin, Cefaloglycin, Cefaloniium, Cefaloridine, Cefalotin, Cefapirin, Cefatrizine, Cefazedone, Cefazaflur, Cefradine, Cefroxadine, Ceftezole, Cefaclor, Cefamandole, Cefminox, Cefonicid, Ceforanide, Cefotiam, Cefprozil, Cefbuperazone, Cefuroxime, Cefuzonam, Cefoxitin, Cefotetan, Cefmetazole, Loracarbef, Cefixime, Ceftazidime, Ceftriaxone, Cefcapene, Cefdaloxime, Cefdinir, Cefditoren, Cefetamet, Cefmenoxime, Cefodizime, Cefoperazone, Cefotaxime, Cefpimizole, Cefpiramide, Cefpodoxime, Cefsulodin, Cefteram, Ceftibuten, Ceftiolene, Ceftizoxime, Flomoxef, Latamoxef, Cefepime, Cefozopran, Cefpirome, Cefquinome, Ceftobiprole, Ceftaroline, CXA-101, RWJ-54428, MC-04,546, ME1036, BAL30072, SYN 2416, Ceftiofur, Cefquinome, Cefovecin, Aztreonam, Tigemonam, Carumonam, RWJ-442831, RWJ-333441, or RWJ-333442.

In some embodiments, the β-lactam includes Ceftazidime, Doripenem, Ertapenem, Imipenem, Meropenem, or Panipenem.

Some embodiments include a pharmaceutical composition comprising a therapeutically effective amount of any one of the foregoing compounds and a pharmaceutically acceptable excipient.

In some embodiments, the β-lactam is selected from Aztreonam, Tigemonam, BAL30072, SYN 2416, or Carumonam.

Administration and Pharmaceutical Compositions

Some embodiments include pharmaceutical compositions comprising: (a) a safe and therapeutically effective amount of compound I, or its corresponding enantiomer, diastereoisomer or tautomer, or pharmaceutically acceptable salt; (b) a carbapenem antibacterial agent, and (c) a pharmaceutically acceptable carrier.

Compound I and the carbapenem antibacterial agent are administered at a therapeutically effective dosage, e.g., a dosage sufficient to provide treatment for the disease states previously described. While human dosage levels have yet to be optimized for the compounds of the preferred embodiments, generally, a daily dose for Compound I is from about 0.1 mg/kg to about 1000 mg/kg or more of body weight, from about 0.5 mg/kg or less to about 500 mg/kg, from about 1.0 mg/kg to about 300 mg/kg of body weight, or from about 1.5 mg/kg to about 150 mg/kg of body weight. Thus, for administration to a 70 kg person, the dosage range would be from about 7 mg per day to about 70,000 mg per day, from about 35 mg per day or less to about 35,000 mg per day or more, from about 70 mg per day to about 21,000 mg per day, from about 105 mg per day to about 10,500 mg per day. The amount of Compound I and the carbapenem antibacterial agent administered will, of course, be dependent on the subject and disease state being treated, the severity of the affliction, the manner and schedule of administration and the judgment of the prescribing physician.

Administration of the combination comprising Compound I or its corresponding enantiomer, diastereoisomer, tautomer, or the pharmaceutically acceptable salt thereof and the carbapenem antibacterial agent can be via any of the accepted modes of administration for agents that serve similar utilities including, but not limited to, orally, subcutaneously, intravenously, intranasally, topically, transdermally, intraperitoneally, intramuscularly, intrapulmonarily, vaginally, rectally, or intraocularly. Oral and parenteral administrations are customary in treating the indications that are the subject of the preferred embodiments.

Compound I and the carbapenem antibacterial agent as described above can be formulated into pharmaceutical compositions for use in treatment of these conditions. Standard pharmaceutical formulation techniques are used, such as those disclosed in Remington's The Science and Practice of Pharmacy, 21st Ed., Lippincott Williams & Wilkins (2005), incorporated by reference in its entirety.

In addition to Compound I and the carbapenem antibacterial agent as described above, some embodiments include compositions containing a pharmaceutically-acceptable carrier. The term "pharmaceutically-acceptable carrier", as used herein, means one or more compatible solid or liquid filler diluents or encapsulating substances, which are suitable for administration to a mammal. The term "compatible", as used herein, means that the components of the composition are capable of being commingled with the subject compound, and with each other, in a manner such that there is no interaction, which would substantially reduce the pharmaceutical efficacy of the composition under ordinary use situations. Pharmaceutically-acceptable carriers must, of course, be of sufficiently high purity and sufficiently low toxicity to render them suitable for administration preferably to an animal, preferably mammal being treated.

Some examples of substances, which can serve as pharmaceutically-acceptable carriers or components thereof, are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the combination is basically determined by the way the combination is to be administered.

The compositions described herein are preferably provided in unit dosage form. As used herein, a "unit dosage form" is a composition containing an amount of a compound that is suitable for administration to an animal, preferably mammal subject, in a single dose, according to good medical practice. The preparation of a single or unit dosage form however, does not imply that the dosage form is administered once per day or once per course of therapy. Such dosage forms are contemplated to be administered once, twice, thrice or more per day and may be administered as infusion over a period of time (e.g., from about 30 minutes to about 2-6 hours), or administered as a continuous infusion, and may be given more than once during a course of therapy, though a single administration is not specifically excluded. The skilled artisan will recognize that the formulation does not specifically contemplate the entire course of therapy and such decisions are left for those skilled in the art of treatment rather than formulation.

The compositions useful as described above may be in any of a variety of suitable forms for a variety of routes for administration, for example, for oral, nasal, rectal, topical (including transdermal), ocular, intracerebral, intracranial, intrathecal, intra-arterial, intravenous, intramuscular, or other parental routes of administration. The skilled artisan will appreciate that oral and nasal compositions comprise compositions that are administered by inhalation, and made using available methodologies. Depending upon the particular route of administration desired, a variety of pharmaceutically-acceptable carriers well-known in the art may be used. Pharmaceutically-acceptable carriers include, for example, solid or liquid fillers, diluents, hydrotropies, surface-active agents, and encapsulating substances. Optional pharmaceutically-active materials may be included, which do not substantially interfere with the inhibitory activity of the compound. The amount of carrier employed in conjunction with the compound is sufficient to provide a practical quantity of material for administration per unit dose of the compound. Techniques and compositions for making dosage forms useful in the methods described herein are described in the following references, all incorporated by reference herein: Modern Pharmaceutics, 4th Ed., Chapters 9 and 10 (Banker & Rhodes, editors, 2002); Lieberman et al., Pharmaceutical Dosage Forms: Tablets (1989); and Ansel, Introduction to Pharmaceutical Dosage Forms 8th Edition (2004). In some embodiments, the pharmaceutical compositions are administered intravenously. In some embodiments, the pharmaceutical compositions are administered orally. In some other embodiments, the pharmaceutical compositions are administered intraperitoneally.

Various oral dosage forms can be used, including such solid forms as tablets, capsules, granules and bulk powders. These oral forms comprise a safe and effective amount, usually at least about 5%, with a maximum of about 90%, of the compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration is well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit coatings, waxes and shellac.

Compositions described herein may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

A liquid composition, which is formulated for topical ophthalmic use, is formulated such that it can be administered topically to the eye. The comfort should be maximized as much as possible, although sometimes formulation considerations (e.g. drug stability) may necessitate less than optimal comfort. In the case that comfort cannot be maximized, the liquid should be formulated such that the liquid is tolerable to the patient for topical ophthalmic use. Additionally, an ophthalmically acceptable liquid should either be packaged for single use, or contain a preservative to prevent contamination over multiple uses.

For ophthalmic application, solutions or medicaments are often prepared using a physiological saline solution as a major vehicle. Ophthalmic solutions should preferably be maintained at a comfortable pH with an appropriate buffer system. The formulations may also contain conventional, pharmaceutically acceptable preservatives, stabilizers and surfactants.

Preservatives that may be used in the pharmaceutical compositions disclosed herein include, but are not limited to, benzalkonium chloride, PHMB, chlorobutanol, thimerosal, phenylmercuric, acetate and phenylmercuric nitrate. A useful surfactant is, for example, Tween 80. Likewise, various useful vehicles may be used in the ophthalmic preparations disclosed herein. These vehicles include, but are not limited to, polyvinyl alcohol, povidone, hydroxypropyl methyl cellulose, poloxamers, carboxymethyl cellulose, hydroxyethyl cellulose and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. For many compositions, the pH will be between 4 and 9. Accordingly, buffers include acetate buffers, citrate buffers, phosphate buffers and borate buffers. Acids or bases may be used to adjust the pH of these formulations as needed.

In a similar vein, an ophthalmically acceptable antioxidant includes, but is not limited to, sodium metabisulfite, sodium thiosulfate, acetylcysteine, butylated hydroxyanisole and butylated hydroxytoluene.

Other excipient components, which may be included in the ophthalmic preparations, are chelating agents. A useful chelating agent is edetate disodium, although other chelating agents may also be used in place or in conjunction with it.

For topical use, creams, ointments, gels, solutions or suspensions, etc., containing the compound disclosed herein are employed. Topical formulations may generally be comprised of a pharmaceutical carrier, co-solvent, emulsifier, penetration enhancer, preservative system, and emollient.

For intravenous administration, the compounds and compositions described herein may be dissolved or dispersed in a pharmaceutically acceptable diluent, such as a saline or dextrose solution. Suitable excipients may be included to achieve the desired pH, including but not limited to NaOH, sodium carbonate, sodium acetate, HCl, and citric acid. In various embodiments, the pH of the final composition ranges from 2 to 8, or preferably from 4 to 7. Antioxidant excipients may include sodium bisulfite, acetone sodium bisulfite, sodium formaldehyde, sulfoxylate, thiourea, and EDTA. Other non-limiting examples of suitable excipients found in the final intravenous composition may include sodium or potassium phosphates, citric acid, tartaric acid, gelatin, and carbohydrates such as dextrose, mannitol, and dextran. Further acceptable excipients are described in Powell, et al., Compendium of Excipients for Parenteral Formulations, *PDA J Pharm Sci and Tech* 1998, 52 238-311 and Nema et al., Excipients and Their Role in Approved Injectable Products: Current Usage and Future Directions, *PDA J Pharm Sci and Tech* 2011, 65 287-332, both of which are incorporated herein by reference in their entirety. Antimicrobial agents may also be included to achieve a bacteriostatic or fungistatic solution, including but not limited to phenylmercuric nitrate, thimerosal, benzethonium chloride, benzalkonium chloride, phenol, cresol, and chlorobutanol.

The resulting composition may be infused into the patient over a period of time. In various embodiments, the infusion time ranges from 5 minutes to continuous infusion, from 10 minutes to 8 hours, from 30 minutes to 4 hours, and from 1 hour to 3 hours. In one embodiment, the drug is infused over a 3 hour period. The infusion may be repeated at the desired dose interval, which may include, for example, 6 hours, 8 hours, 12 hours, or 24 hours.

The compositions for intravenous administration may be provided to caregivers in the form of one more solids that are reconstituted with a suitable diluent such as sterile water, saline or dextrose in water shortly prior to administration. Reconstituted concentrated solutions may be further diluted into a parenteral solutions having a volume of from about 25 to about 1000 ml, from about 30 ml to about 500 ml, or from about 50 ml to about 250 ml. In other embodiments, the compositions are provided in solution ready to administer parenterally. In still other embodiments, the compositions are provided in a solution that is further diluted prior to administration. In embodiments that include administering a combination of a compound described herein and another agent, the combination may be provided to caregivers as a mixture, or the caregivers may mix the two agents prior to administration, or the two agents may be administered separately.

The actual dose of the active compounds described herein depends on the specific compound, and on the condition to be treated; the selection of the appropriate dose is well within the knowledge of the skilled artisan.

Kits for Intravenous Administration

Some embodiments include a kit comprising Compound I and a carbapenem antibacterial agent. In some embodiments, the carbapenem antibacterial agent is selected from the group consisting of Imipenem, Biapenem, Doripenem, Meropenem, and Ertapenem. In one embodiment, the carbapenem antibacterial agent is Biapenem.

In one embodiment, both components are provided in a single sterile container. In the case of solids for reconstitution, the agents may be pre-blended and added to the container simultaneously or may be dry-powder filled into the container in two separate steps. In some embodiments, the solids are sterile crystalline products. In other embodiment, the solids are lyophiles. In one embodiment, both components are lyophilized together. Non-limiting examples of agents to aid in lyophilization include sodium or potassium phosphates, citric acid, tartaric acid, gelatin, and carbohydrates such as dextrose, mannitol, and dextran. One embodiment includes non-sterile solids that are irradiated either before or after introduction into the container.

In the case of a liquid, the agents may be dissolved or dispersed in a diluent ready for administration. In another embodiment, the solution or dispersion may be further diluted prior to administration. Some embodiments include providing the liquid in an IV bag. The liquid may be frozen to improve stability.

In one embodiment, the container includes other ingredients such as a pH adjuster, a solubilizing agent, or a dispersing agent. Non-limiting examples of pH adjusters include NaOH, sodium carbonate, sodium acetate, HCl, and citric acid.

The molar ratio of compound I described herein to additional agent (e.g., antibacterial agent) may be from about 20:1 to 1:20, 8:1 to 1:8, 5:1 to 1:5, 3:1 to 1:3, 2:1 to 1:2, or about 1:1. In various embodiments the amount of compound I described herein may be from 100 mg to 10 g, 500 mg to 5 g, or about 2 g. Similarly, in various embodiments the amount of additional agent may be from 100 mg to 5 g, 500 mg to 2 g, or about 1 g.

In an alternative embodiment, the two components may be provided in separate containers. Each container may include a solid, solution, or dispersion. In such embodiments, the two containers may be provided in a single package or may be provided separately. In one embodiment, the compound described herein is provided as a solution while the additional agent (e.g., antibacterial agent) is provided as a solid ready for reconstitution. In one such embodiment, the solution of the compound described herein is used as the diluent to reconstitute the other agent.

In some embodiments, the kit may comprise comprises one or more additional medicaments selected from an antibacterial agent, antifungal agent, an antiviral agent, an anti-inflammatory agent, or an anti-allergic agent. The additional medicaments can be prepared in the same way as described above.

The following examples will further describe the present invention, and are used for the purposes of illustration only, and should not be considered as limiting.

EXAMPLES

General Procedures

Materials used in preparing Compound I and its enantiomer, diastereoisomer or tautomer, or pharmaceutically acceptable salt described herein may be made by known methods or are commercially available. It will be apparent to the skilled artisan that methods for preparing precursors and functionality related to the compounds claimed herein are generally described in the literature including, for example, procedures described in U.S. Pat. No. 7,271,186 and WO 2009/064414, each of which is incorporated by reference in its entirety. In these reactions, it is also possible to make use of variants which are themselves known to those of ordinary skill in this art, but are not mentioned in greater detail. The skilled artisan given the literature and this disclosure is well equipped to prepare any of the compounds.

Trademarks used herein are examples only and reflect illustrative materials used at the time of the invention. The skilled artisan will recognize that variations in lot, manufacturing processes, and the like, are expected. Hence the examples, and the trademarks used in them are non-limiting, and they are not intended to be limiting, but are merely an illustration of how a skilled artisan may choose to perform one or more of the embodiments of the invention.

Example 1

Example 1 provides a summary of three pharmacokinetic studies Compound I conducted in Swiss-webster mice. The pharmacokinetics of 5 mg/kg, 15 mg/kg and 50 mg/kg of Compound I via the intraperitoneal route were discussed.

Materials and Methods

Compound I was prepared using the method described in the U.S. Publication 2012/0040932 A1. 100 mg of Compound I was dissolved in 30% 1N NaOH to ~pH 5.0 as a stock solution. Compound I was further diluted in 0.9% saline to achieve target concentrations.

The specifications for animals used on this study were as follows:

Species: Mouse
Strain: CFW (Swiss)
Gender: Female
Source: Harlan Laboratories (Livermore, Calif.)
Number of Animals: 33 for each dose
Body Weight Range: 18-22 g at the start of the study Upon receipt, animals were housed 4 per cage in a room with a controlled environment and were acclimated to laboratory conditions for at least 24 hours prior to the start of dosing. Animals were provided food and water ad libitum. The health status of the animals was determined during the acclimation period and unhealthy animals were not placed on study. Each animal was identified by marking their tails with indelible ink and each cage was identified by animal, group, and study number.

After acclimation, mice were administered a single intraperitoneal dose of Compound I at 5, 15, and 50 mg/kg. Groups of three mice were sacrificed at 0.08, 0.16, 0.25, 0.33, 0.5, 0.75, 1.0, 2.0, 3.0, and 4.0 h after dosing. Blood samples (one sample per animal) were collected by cardiac puncture in a heparin containing tube. Blood samples were centrifuged within 5 min of collection at 12000 g for 5 min to obtain plasma. The plasma samples were stored on −80° C. until analyzed.

Compound I standard curves were prepared in plasma from 0.1 to 100 μg/mL. 50 μl aliquots of sample were placed in 1.5 mL microcentrifuge tubes. 20 μl of Compound II (10 μg/mL) was added as internal standard to each sample or standard. 20 μl of 30% trichloroacetic acid was then added to each sample or standard. The samples were mixed using a vortex mixer centrifuged for 10 min at 15,000 RPM using a tabletop centrifuge. The supernatant (approx. 120 μl) was removed and added to 100 μl of water in a 96-well plate. The samples were mixed again using a vortex mixer. 10 μl of each sample was injected onto an HPLC-MS for quantification.

The HPLC-MS conditions for plasma analysis are as follows:

Column: Phenomenex Fusion-RP or equivalent reversed-phase column, 5 um, 50×2 mm.

Flow rate: 0.6 mL/min.

Mobile phase A: 0.1% formic acid in water.

Mobile phase B: 0.1% formic acid in acetonitrile.

Gradient: 5-60% B in 1.5 min.

Mass spectrometer: Negative ion mode with electrospray ionization.

MS/MS: Compound I-Q1-m/e=296, Q3-m/e=234.

Compound II-Q1-m/e=331, Q3-m/e=201.

Plasma concentrations were fit using a one compartment IV infusion model (WinNonlinVersion 5.3, Pharsight Corp, and Mountain View, Calif.).

The study groups, dose and dose route are illustrated in the table below:

| Dose (mg/kg) | Time Points(hr) | Number of Animal per Timepoint | Route of Administration |
|---|---|---|---|
| 5 | 0.08, 0.16, 0.25, 0.33, 0.5, 0.75, 1.0, 2.0, 3.0, 4.0 | 3 | Intraperitoneal |
| 15 | 0.08, 0.16, 0.25, 0.33, 0.5, 0.75, 1.0, 2.0, 3.0, 4.0 | 3 | Intraperitoneal |
| 50 | 0.08, 0.16, 0.25, 0.33, 0.5, 0.75, 1.0, 2.0, 3.0, 4.0 | 3 | Intraperitoneal |

Results

The summary of the plasma pharmacokinetics of intraperitoneal dose of 5, 15, and 50 mg/kg of Compound I in Swiss Webster mice are shown in FIG. 1 and Table 1.

TABLE 1

Plasma Pharmacokinetic Parameters of Compound I in Swiss-Webster Mice

| Dose (mg/kg) | Cl (l/hr/kg) | AUC (hr*mg/kg) | Cmax (mg/l) | $T_{1/2}$ (h) |
|---|---|---|---|---|
| 5 | 1.61 | 3.1 | 8.26 | 0.16 |
| 15 | 1.8 | 8.3 | 19.5 | 0.2 |
| 50 | 1.6 | 31.35 | 67.09 | 0.25 |

The plasma standard curves of all three studies were linear and used to determine the plasma concentrations. The plasma standard curve and concentrations are shown in Table 2-7. The pharmacokinetic profile of Compound I was assessed in mice after single intraperitoneal doses of 5, 15, and 50 mg/kg. Data indicate that Compound I has a linear PK in Swiss-Webster mice over the dose range of 5 to 50 mg/kg.

TABLE 2

Plasma Standard Curve for Pharmacokinetics of 5 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
|---|---|---|---|---|---|---|
| wash | 0 | N/A | 0 | #DIV/0! | 0.00E+00 | #DIV/0! |
| ctl rat plasma | 0 | N/A | 0 | #DIV/0! | 0.00E+00 | #DIV/0! |
| ctl rat plasma w/ Gati | 0 | N/A | 0 | 0.00E+00 | 1.63E+04 | No Peak |
| 0.1 ug/ml m.p. Compound I | 5910 | N/A | 1.62 | 3.71E−01 | 1.59E+04 | 0.152 |
| 0.2 ug/ml m.p. Compound I | 12100 | N/A | 1.62 | 6.41E−01 | 1.88E+04 | 0.264 |
| 0.5 ug/ml m.p. Compound I | 32600 | N/A | 1.59 | 1.67E+00 | 1.95E+04 | 0.691 |
| 1 ug/ml m.p. Compound I | 63500 | 1 | 1.63 | 2.81E+00 | 2.26E+04 | 1.16 |
| 2 ug/ml m.p. Compound I | 122000 | 2 | 1.62 | 5.47E+00 | 2.23E+04 | 2.28 |
| 5 ug/ml m.p. Compound I | 326000 | N/A | 1.63 | 1.43E+01 | 2.28E+04 | 6.03 |
| 10 ug/ml m.p. Compound I | 657000 | 10 | 1.63 | 2.69E+01 | 2.44E+04 | 11.5 |
| 20 ug/ml m.p. Compound I | 1280000 | 20 | 1.63 | 5.06E+01 | 2.52E+04 | 22.3 |
| 50 ug/ml m.p. Compound I | 2780000 | 50 | 1.63 | 1.18E+02 | 2.35E+04 | 58.1 |
| 100 ug/ml m.p. Compound I | 4890000 | 100 | 1.63 | 1.91E+02 | 2.56E+04 | 114 |
| wash | 17300 | N/A | 1.57 | #DIV/0! | 0.00E+00 | #DIV/0! |

TABLE 3

Plasma Concentrations for Pharmacokinetics of 5 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
|---|---|---|---|---|---|---|
| m.p. 1.1 no dil. (5 mg/kg) | 405000 | N/A | 1.64 | 1.37E+01 | 2.96E+04 | 5.77 |
| m.p. 1.2 no dil. (5 mg/kg) | 368000 | N/A | 1.63 | 1.15E+01 | 3.19E+04 | 4.84 |
| m.p. 1.3n0 dil. (5 mg/kg) | 423000 | N/A | 1.63 | 1.33E+01 | 3.19E+04 | 5.58 |
| m.p. 2.1 no dil. (5 mg/kg) | 687000 | N/A | 1.63 | 2.27E+01 | 3.02E+04 | 9.68 |
| m.p. 2.2 no dil. (5 mg/kg) | 549000 | N/A | 1.63 | 1.75E+01 | 3.13E+04 | 7.41 |
| m.p. 2.3 no dil. (5 mg/kg) | 276000 | N/A | 1.62 | 8.36E+00 | 3.30E+04 | 3.49 |
| m.p. 3.1 no dil. (5 mg/kg) | 662000 | N/A | 1.62 | 2.14E+01 | 3.10E+04 | 9.08 |

TABLE 3-continued

Plasma Concentrations for Pharmacokinetics of 5 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
|---|---|---|---|---|---|---|
| m.p. 3.2 no dil. (5 mg/kg) | 548000 | N/A | 1.63 | 1.76E+01 | 3.12E+04 | 7.43 |
| m.p. 3.3 no dil. (5 mg/kg) | 279000 | N/A | 1.62 | 9.07E+00 | 3.08E+04 | 3.8 |
| m.p. 4.1 no dil. (5 mg/kg) | 243000 | N/A | 1.61 | 8.07E+00 | 3.02E+04 | 3.37 |
| m.p. 4.2 no dil. (5 mg/kg) | 79100 | N/A | 1.61 | 2.43E+00 | 3.26E+04 | 1.01 |
| m.p. 4.3 no dil. (5 mg/kg) | 139000 | N/A | 1.62 | 4.49E+00 | 3.10E+04 | 3.73 |
| m.p. 5.1 no dil. (5 mg/kg) | 111000 | N/A | 1.62 | 3.74E+00 | 2.98E+04 | 1.55 |
| m.p. 5.2 no dil. (5 mg/kg) | 147000 | N/A | 1.61 | 4.50E+00 | 3.26E+04 | 1.87 |
| m.p. 5.3 no dil. (5 mg/kg) | 102000 | N/A | 1.62 | 3.16E+00 | 3.22E+04 | 1.31 |
| m.p. 6.1 no dil. (5 mg/kg) | 8470 | N/A | 1.61 | 2.69E−01 | 3.14E+04 | 0.110 |
| m.p. 6.2 no dil. (5 mg/kg) | 72300 | N/A | 1.62 | 2.10E+00 | 3.44E+04 | 0.872 |
| m.p. 6.3 no dil. (5 mg/kg) | 35900 | N/A | 1.61 | 1.11E+00 | 3.22E+04 | 0.461 |
| m.p. 7.1 no dil. (5 mg/kg) | 42600 | N/A | 1.62 | 1.33E+00 | 3.19E+04 | 0.551 |
| m.p. 7.2 no dil. (5 mg/kg) | 17400 | N/A | 1.6 | 5.17E−01 | 3.36E+04 | 0.213 |
| m.p. 7.3 no dil. (5 mg/kg) | 35800 | N/A | 1.61 | 1.11E+00 | 3.24E+04 | 0.457 |
| m.p. 8.1 no dil. (5 mg/kg) | 7390 | N/A | 1.61 | 2.21E−01 | 3.34E+04 | 0.0898 |
| m.p. 8.2 no dil. (5 mg/kg) | 3170 | N/A | 1.58 | 1.02E−01 | 3.10E+04 | 0.0404 |
| m.p. 8.3 no dil. (5 mg/kg) | 3330 | N/A | 1.6 | 1.11E−01 | 3.00E+04 | 0.0440 |
| m.p. 9.1 no dil. (5 mg/kg) | 938 | N/A | 1.57 | 2.96E−02 | 3.17E+04 | 0.0103 |
| m.p. 9.2 no dil. (5 mg/kg) | 2860 | N/A | 1.62 | 9.02E−02 | 3.17E+04 | 0.0354 |
| m.p. 9.3 no dil. (5 mg/kg) | 805 | N/A | 1.6 | 2.42E−02 | 3.32E+04 | 0.00806 |
| m.p. 10.1 no dil. (5 mg/kg) | 387 | N/A | 1.55 | 1.37E−02 | 2.82E+04 | 0.00371 |
| m.p. 10.2 no dil. (5 mg/kg) | 584 | N/A | 1.61 | 1.87E−02 | 3.12E+04 | 0.00577 |
| m.p. 10.3 no dil. (5 mg/kg) | 463 | N/A | 1.64 | 1.49E−02 | 3.12E+04 | 0.00418 |

TABLE 4

Plasma Standard Curve for Pharmacokinetics of 15 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
|---|---|---|---|---|---|---|
| wash | 0 | N/A | 0 | #DIV/0! | 0.00E+00 | #DIV/0! |
| ctl rat plasma | 0 | N/A | 0 | #DIV/0! | 0.00E+00 | #DIV/0! |
| ctl rat plasma w/ Gati | 0 | N/A | 0 | 0.00E+00 | 2.88E+04 | No Peak |
| 0.1 ug/ml m.p. Compound I | 9010 | N/A | 1.58 | 3.18E−01 | 2.84E+04 | 0.130 |
| 0.2 ug/ml m.p. Compound I | 14400 | 0.2 | 1.6 | 4.93E−01 | 2.93E+04 | 0.215 |
| 0.5 ug/ml m.p. Compound I | 32300 | 0.5 | 1.6 | 1.14E+00 | 2.84E+04 | 0.531 |
| 1 ug/ml m.p. Compound I | 61500 | 1 | 1.6 | 2.14E+00 | 2.87E+04 | 1.02 |
| 2 ug/ml m.p. Compound I | 116000 | 2 | 1.6 | 4.10E+00 | 2.83E+04 | 1.98 |
| 5 ug/ml m.p. Compound I | 304000 | 5 | 1.6 | 1.08E+01 | 2.82E+04 | 5.29 |
| 10 ug/ml m.p. Compound I | 610000 | 10 | 1.6 | 2.09E+01 | 2.92E+04 | 10.4 |
| 20 ug/ml m.p. Compound I | 1100000 | 20 | 1.6 | 3.80E+01 | 2.89E+04 | 19.4 |
| 50 ug/ml m.p. Compound I | 2510000 | 50 | 1.6 | 9.07E+01 | 2.77E+04 | 50.6 |
| 100 ug/ml m.p. Compound I | 4390000 | 100 | 1.6 | 1.58E+02 | 2.78E+04 | 105 |
| wash | 16500 | N/A | 1.53 | #DIV/0! | 0.00E+00 | #DIV/0! |

TABLE 5

Plasma Concentrations for Pharmacokinetics of 15 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
|---|---|---|---|---|---|---|
| m.p. 1.1 no dil. (15 mg/kg) | 570000 | N/A | 1.61 | 1.95E+01 | 2.93E+04 | 9.67 |
| m.p. 1.2 no dil. (15 mg/kg) | 4800000 | N/A | 1.6 | 1.60E+02 | 3.00E+04 | |
| m.p. 1.3 no dil. (15 mg/kg) | 983000 | N/A | 1.6 | 3.30E+01 | 2.98E+04 | 16.7 |
| m.p. 2.1 no dil. (15 mg/kg) | 961000 | N/A | 1.61 | 3.07E+01 | 3.13E+04 | 15.5 |
| m.p. 2.2 no dil. (15 mg/kg) | 517000 | N/A | 1.61 | 1.73E+01 | 2.98E+04 | 8.58 |
| m.p. 2.3 no dil. (15 mg/kg) | 19500 | N/A | 1.56 | 6.42E−01 | 3.04E+04 | |
| m.p. 3.1 no dil. (15 mg/kg) | 586000 | N/A | 1.61 | 1.92E+01 | 3.05E+04 | 9.53 |

TABLE 5-continued

Plasma Concentrations for Pharmacokinetics of 15 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
| --- | --- | --- | --- | --- | --- | --- |
| m.p. 3.2 no dil. (15 mg/kg) | 371000 | N/A | 1.61 | 1.14E+01 | 3.26E+04 | 5.59 |
| m.p. 3.3 no dil. (15 mg/kg) | 865000 | N/A | 1.6 | 2.84E+01 | 3.05E+04 | 14.3 |
| m.p. 4.1 no dil. (15 mg/kg) | 348000 | N/A | 1.61 | 1.14E+01 | 3.04E+04 | 5.6 |
| m.p. 4.2 no dil. (15 mg/kg) | 756000 | N/A | 1.61 | 2.46E+01 | 3.08E+04 | 12.3 |
| m.p. 4.3 no dil. (15 mg/kg) | 284000 | N/A | 1.61 | 9.08E+00 | 3.13E+04 | 4.44 |
| m.p. 5.1 no dil. (15 mg/kg) | 269000 | N/A | 1.6 | 8.34E+00 | 3.23E+04 | 4.07 |
| m.p. 5.2 no dil. (15 mg/kg) | 218000 | N/A | 1.59 | 7.24E+00 | 3.02E+04 | 3.52 |
| m.p. 5.3 no dil. (15 mg/kg) | 444000 | N/A | 1.59 | 1.43E+01 | 3.11E+04 | 7.05 |
| m.p. 6.1 no dil. (15 mg/kg) | 3150 | N/A | 1.57 | 1.03E−01 | 3.04E+04 | 0.0261 |
| m.p. 6.2 no dil. (15 mg/kg) | 241000 | N/A | 1.61 | 7.64E+00 | 3.15E+04 | 3.72 |
| m.p. 6.3 no dil. (15 mg/kg) | 190000 | N/A | 1.61 | 6.15E+00 | 3.09E+04 | 2.99 |
| m.p. 7.1 no dil. (15 mg/kg) | 31700 | N/A | 1.56 | 1.15E+00 | 2.76E+04 | 0.534 |
| m.p. 7.2 no dil. (15 mg/kg) | 146000 | N/A | 1.61 | 4.70E+00 | 3.11E+04 | 2.28 |
| m.p. 7.3 no dil. (15 mg/kg) | 102000 | N/A | 1.6 | 3.36E+00 | 3.03E+04 | 1.61 |
| m.p. 8.1 no dil. (15 mg/kg) | 9560 | N/A | 1.58 | 3.09E−01 | 3.09E+04 | 0.126 |
| m.p. 8.2 no dil. (15 mg/kg) | 10000 | N/A | 1.6 | 3.48E−01 | 2.88E+04 | 0.145 |
| m.p. 8.3 no dil. (15 mg/kg) | 7670 | N/A | 1.6 | 2.40E−01 | 3.19E+04 | 0.0926 |
| m.p. 9.1 no dil. (15 mg/kg) | 1130 | N/A | 1.62 | 3.77E−02 | 2.99E+04 | <0 |
| m.p. 9.2 no dil. (15 mg/kg) | 1290 | N/A | 1.55 | 3.98E−02 | 3.25E+04 | <0 |
| m.p. 9.3 no dil. (15 mg/kg) | 2700 | N/A | 1.56 | 8.63E−02 | 3.13E+04 | 0.0178 |
| m.p. 10.1 no dil. (15 mg/kg) | 546 | N/A | 1.6 | 1.87E−02 | 2.91E+04 | <0 |
| m.p. 10.2 no dil. (15 mg/kg) | 1030 | N/A | 1.6 | 3.29E−02 | 3.12E+04 | <0 |
| m.p. 10.3 no dil. (15 mg/kg) | 752 | N/A | 1.6 | 2.54E−02 | 2.97E+04 | <0 |

TABLE 6

Plasma Standard Curve for Pharmacokinetics of 50 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
| --- | --- | --- | --- | --- | --- | --- |
| wash | 0 | N/A | 0 | #DIV/0! | 0.00E+00 | #DIV/0! |
| ctl rat plasma | 0 | N/A | 0 | #DIV/0! | 0.00E+00 | #DIV/0! |
| ctl mt plasma w/ Gati | 0 | N/A | 0 | 0.00E+00 | 2.27E+04 | No Peak |
| 0.1 ug/ml m.p. Compound I | 7570 | 0.1 | 1.55 | 3.57E−01 | 2.12E+04 | 0.0994 |
| 0.2 ug/ml m.p. Compound I | 15600 | 0.2 | 1.55 | 7.12E−01 | 2.19E+04 | 0.213 |
| 0.5 ug/ml m.p. Compound I | 39500 | 0.5 | 1.55 | 1.76E+00 | 2.24E+04 | 0.549 |
| 1 ug/ml m.p. Compound I | 78300 | 1 | 1.55 | 3.37E+00 | 2.32E+04 | 1.07 |
| 2 ug/ml m.p. Compound I | 159000 | 2 | 1.55 | 6.74E+00 | 2.37E+04 | 2.16 |
| 5 ug/ml m.p. Compound I | 385000 | 5 | 1.55 | 1.57E+01 | 2.45E+04 | 5.16 |
| 10 ug/ml m.p. Compound I | 716000 | 10 | 1.55 | 3.21E+01 | 2.23E+04 | 10.9 |
| 20 ug/ml m.p. Compound I | 1390000 | 20 | 1.57 | 5.82E+01 | 2.39E+04 | 20.9 |
| 50 ug/ml m.p. Compound I | 3000000 | 50 | 1.58 | 1.25E+02 | 2.40E+04 | 56.7 |
| 100 ug/ml m.p. Compound I | 4870000 | N/A | 1.57 | 2.36E+02 | 2.06E+04 | No Intercept |
| wash | 9190 | N/A | 1.5 | #DIV/0! | 0.00E+00 | #DIV/0! |

TABLE 7

Plasma Concentrations for Pharmacokinetics of 50 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
| --- | --- | --- | --- | --- | --- | --- |
| m.p. 1.1 no dil. | 2530000 | N/A | 1.59 | 9.78E+01 | 2.59E+04 | 39.4 |
| m.p. 1.2 no dil. | 2110000 | N/A | 1.6 | 7.15E+01 | 2.95E+04 | 26.6 |
| m.p. 1.3 no dil. | 2350000 | N/A | 1.59 | 8.89E+01 | 2.64E+04 | 34.8 |
| m.p. 2.1 5× dil. (50 mg/kg) | 686000 | N/A | 1.59 | 2.36E+01 | 2.91E+04 | 58.9 |
| m.p. 2.2 5× dil. (50 mg/kg) | 744000 | N/A | 1.59 | 2.58E+01 | 2.89E+04 | 64.7 |
| m.p. 2.3 5× dil. (50 mg/kg) | 673000 | N/A | 1.59 | 2.31E+01 | 2.91E+04 | 57.7 |
| m.p. 3.1 5× dil. (50 mg/kg) | 727000 | N/A | 1.59 | 2.56E+01 | 2.84E+04 | 64.2 |

TABLE 7-continued

Plasma Concentrations for Pharmacokinetics of 50 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
|---|---|---|---|---|---|---|
| m.p. 3.2 5× dil. (50 mg/kg) | 677000 | N/A | 1.59 | 2.27E+01 | 2.98E+04 | 56.8 |
| m.p. 3.3 5× dil. (50 mg/kg) | 751000 | N/A | 1.58 | 2.46E+01 | 3.05E+04 | 61.7 |
| m.p. 4.1 no dil. | 2610000 | N/A | 1.59 | 1.03E+02 | 2.54E+04 | 42.1 |
| m.p. 4.2 5× dil. (50 mg/kg) | 1360000 | N/A | 1.59 | 5.18E+01 | 2.64E+04 | |
| m.p. 4.3 no dil. | 2690000 | N/A | 1.6 | 1.05E+02 | 2.55E+04 | 43.6 |
| m.p. 5.1 no dil. | 2450000 | N/A | 1.6 | 8.87E+01 | 2.76E+04 | 34.7 |
| m.p. 5.2 no dil. (50 mg/kg) | 248000 | N/A | 1.6 | 8.31E+00 | 2.99E+04 | |
| m.p. 5.3 no dil. | 1950000 | N/A | 1.6 | 7.25E+01 | 2.69E+04 | 27.0 |
| m.p. 6.1 no dil. | 1440000 | N/A | 1.59 | 5.38E+01 | 2.68E+04 | 19.1 |
| m.p. 6.2 no dil. | 974000 | N/A | 1.58 | 3.35E+01 | 2.91E+04 | 11.4 |
| m.p. 6.3 no dil. | 1160000 | N/A | 1.59 | 4.32E+01 | 2.70E+04 | 15.0 |
| m.p. 7.1 no dil. | 739000 | N/A | 1.59 | 2.76E+01 | 2.68E+04 | 9.26 |
| m.p. 7.2 no dil. | 206000 | N/A | 1.55 | 7.25E+00 | 2.84E+04 | 2.33 |
| m.p. 7.3 no dil. | 125000 | N/A | 1.59 | 4.40E+00 | 2.85E+04 | 1.40 |
| m.p. 8.1 no dil. | 46300 | N/A | 1.54 | 1.78E+00 | 2.61E+04 | 0.555 |
| m.p. 8.2 no dil. | 111000 | N/A | 1.55 | 4.07E+00 | 2.73E+04 | 1.30 |
| m.p. 8.3 no dil. | 57100 | N/A | 1.55 | 1.86E+00 | 3.07E+04 | 0.582 |
| m.p. 9.1 no dil. | 16300 | N/A | 1.56 | 6.13E−01 | 2.66E+04 | 0.181 |
| m.p. 9.2 no dil. | 11700 | N/A | 1.56 | 4.23E−01 | 2.76E+04 | 0.120 |
| m.p. 9.3 no dil. | 11900 | N/A | 1.54 | 3.75E−01 | 3.18E+04 | 0.105 |
| m.p. 10.1 no dil. | 5360 | N/A | 1.55 | 1.94E−01 | 2.76E+04 | 0.0471 |
| m.p. 10.2 no dil. | 13600 | N/A | 1.56 | 4.92E−01 | 2.77E+04 | 0.143 |
| m.p. 10.3 no dil. | 19000 | N/A | 1.55 | 6.67E−01 | 2.85E+04 | 0.199 |

TABLE 8

Re-assay of Standard Curve and Plasma for Pharmacokinetics of 50 mg/kg of Compound I

| Sample Name | Analyte Peak Area (counts) | Analyte Conc. (ug/mL) | Analyte Retent. Time (min) | Area Ratio | IS Peak Area (counts) | Calc. Conc. (ug/mL) |
|---|---|---|---|---|---|---|
| wash | 0 | N/A | 0 | #DIV/0! | 0.00E+00 | #DIV/0! |
| ctl rat plasma | 0 | N/A | 0 | #DIV/0! | 0.00E+00 | #DIV/0! |
| ctl rat plasma w/Gati | 0 | N/A | 0 | 0.00E+00 | 2.88E+04 | No Peak |
| 0.1 ug/ml m.p. Compound I | 9010 | N/A | 1.58 | 3.18E−01 | 2.84E+04 | 0.13 |
| 0.2 ug/ml m.p. Compound I | 14400 | 0.2 | 1.6 | 4.93E−01 | 2.93E+04 | 0.215 |
| 0.5 ug/ml m.p. Compound I | 32300 | 0.5 | 1.6 | 1.14E+00 | 2.84E+04 | 0.531 |
| 1 ug/ml m.p. Compound I | 61500 | 1 | 1.6 | 2.14E+00 | 2.87E+04 | 1.02 |
| 2 ug/ml m.p. Compound I | 116000 | 2 | 1.6 | 4.10E+00 | 2.83E+04 | 1.98 |
| 5 ug/ml m.p. Compound I | 304000 | 5 | 1.6 | 1.08E+01 | 2.82E+04 | 5.29 |
| 10 ug/ml m.p. Compound I | 610000 | 10 | 1.6 | 2.09E+01 | 2.92E+04 | 10.4 |
| 20 ug/ml m.p. Compound I | 1100000 | 20 | 1.6 | 3.80E+01 | 2.89E+04 | 19.4 |
| 50 ug/ml m.p. Compound I | 2510000 | 50 | 1.6 | 9.07E+01 | 2.77E+04 | 50.6 |
| 100 ug/ml m.p. Compound I | 4390000 | 100 | 1.6 | 1.58E+02 | 2.78E+04 | 105 |
| wash | 16500 | N/A | 1.53 | #DIV/0! | 0.00E+00 | #DIV/0! |
| m.p. 2.1 5× dil. (50 mg/kg) | 686000 | N/A | 1.59 | 2.36E+01 | 2.91E+04 | 58.9 |
| m.p. 2.2 5× dil. (50 mg/kg) | 744000 | N/A | 1.59 | 2.58E+01 | 2.89E+04 | 64.7 |
| m.p. 2.3 5× dil. (50 mg/kg) | 673000 | N/A | 1.59 | 2.31E+01 | 2.91E+04 | 57.7 |
| m.p. 3.1 5× dil. (50 mg/kg) | 727000 | N/A | 1.59 | 2.56E+01 | 2.84E+04 | 64.2 |
| m.p. 3.2 5× dil. (50 mg/kg) | 677000 | N/A | 1.59 | 2.27E+01 | 2.98E+04 | 56.8 |
| m.p. 3.3 5× dil. (50 mg/kg) | 751000 | N/A | 1.58 | 2.46E+01 | 3.05E+04 | 61.7 |
| m.p. 4.2 5× dil. (50 mg/kg) | 1360000 | N/A | 1.59 | 5.18E+01 | 2.64E+04 | 135 |
| m.p. 5.2 5× dil. (50 mg/kg) | 248000 | N/A | 1.6 | 8.31E+00 | 2.99E+04 | 4.06 |

Example 2

Example 2 provides a summary of two pharmacokinetic studies of Biapenem conducted in Swiss-webster mice. The pharmacokinetics of 100 mg/kg and 25 mg/kg of Biapenem via the intraperitoneal route was discussed below.

Materials and Methods

Biapenem power was purchased from Hisun Pharmaceuticals. 20 mg of Biapenem was dissolved in 0.1 M $NaH_2PO_4$ for a basic stock solution. For animal studies, this stock solution was further diluted in 0.9% saline to the appropriate concentration.

The specifications for animals used on this study were as follows:
  Species: Mouse
  Strain: CFW (Swiss)
  Gender: Female
  Source: Harlan Laboratories (Livermore, Calif.)
  Number of Animals: 33 for each dose
  Body Weight Range: 18-22 g at the start of the study Upon receipt, animals were housed 4 per cage in a room with a controlled environment and were acclimated to laboratory conditions for at least 24 hours prior to the start of dosing. Animals were provided food and water ad libitum. The health status of the animals was determined during the acclimation period and unhealthy animals were not placed on study. Each animal was identified by marking their tails with indelible ink and each cage was identified by animal, group, and study number.

After acclimation, mice were administered a single intraperitoneal dose of biapenem at 25 or 100 mg/kg. Groups of three mice were sacrificed at 0.08, 0.17, 0.25, 0.33, 0.5, 0.75, 1.0, 3.0, and 6.0 h after dosing. Blood samples (one sample per animal) were collected by cardiac puncture in a heparin containing tube. The collected heparin tubes were centrifuged within 5 min of collection at 12000 g for 5 min to obtain plasma. The plasma samples were stored on −80° C. until analyzed.

Biapenem standard curves were prepared in 50% plasma-50% 1M MOPS buffer, pH=7.4 from 1 to 250 ug/mL. 20 uL of sample or standard was added into a 96-well deep well plate. Then 500 uL of 10% water-45% methanol-45% acetonitrile containing 2 ug/mL of meropenem was used as an internal standard. The plate was vortexed for 15 min. at 3,000 RPM. 50 uL of supernatant was removed and added 300 uL of water. 10 uL of samples were injected onto an HPLC-MS system for quantification.

The HPLC-MS conditions for the Biapenem plasma analysis are as follows:
  Column: Supelco Discovery HS F5 or equivalent pentafluorophenyl column, 5 um, 50×2.1 mm.
  Flow rate: 0.6 mL/min.
  Mobile phase A: 0.1% formic acid in water.
  Mobile phase B: 0.1% formic acid in acetonitrile.
  Gradient: 5-70% B in 1.9 min.
  Mass spectrometer: Positive ion mode with electrospray ionization.
  MS/MS: Biapenem-Q1-m/e=350.8, Q3-m/e=110.1.
    meropenem-Q1-m/e=384.1, Q3-m/e=141.1.

Serum concentrations were determined using HPLC. Serum concentrations were fit by using Non-compartmental model of WinNonlin Software (Pharsight. Version 5.3, Mountain View, Calif.).

The study groups, dose and dose route are illustrated in the table below:

| Dose (mg/kg) | Time Points(hr) | Number of Animal per Timepoint | Route of Administration |
|---|---|---|---|
| 25 | 0.08, 0.16, 0.25, 0.33, 0.5, 0.75, 1.0, 2.0, 3.0, 4.0 | 3 | Intraperitoneal |
| 100 | 0.08, 0.16, 0.25, 0.33, 0.5, 0.75, 1.0, 2.0, 3.0, 4.0 | 3 | Intraperitoneal |

Results

Figure 2:
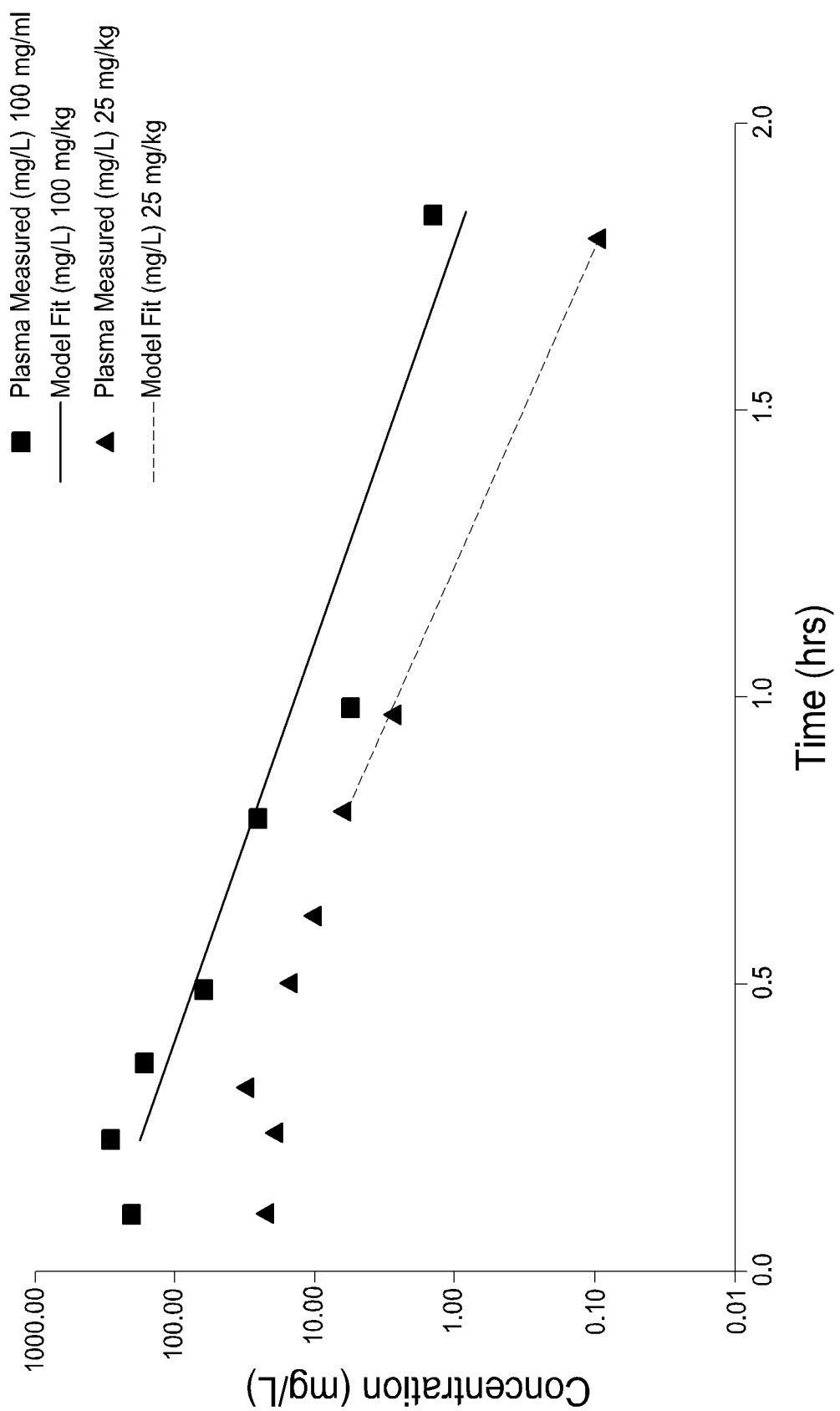
FIG. 2 is a graph depicting the plasma concentration profile of 25 or 100 mg/kg Biapenem as a function of time after administration to Swiss Webster mice.
Figure 3:
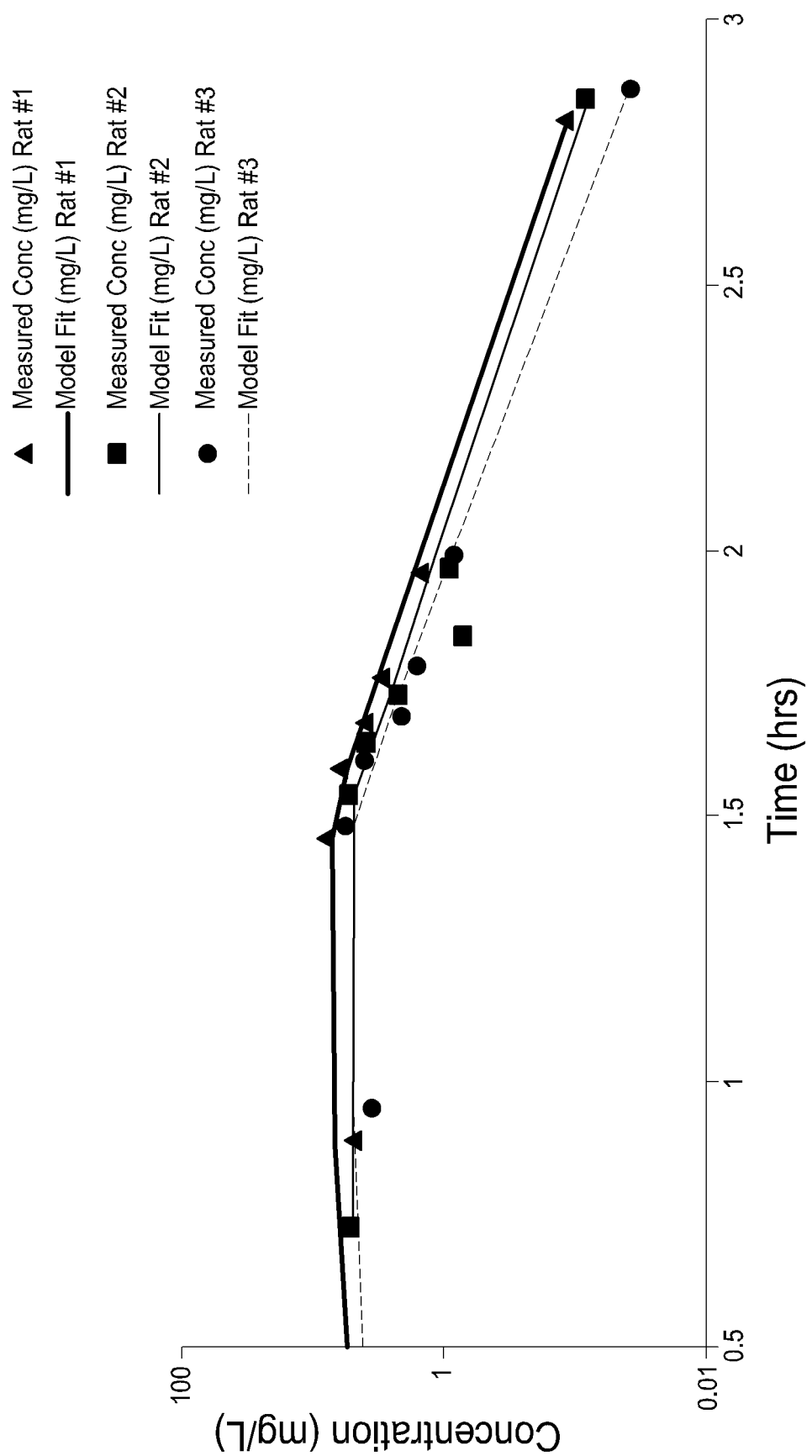
FIG. 3 is a graph depicting the plasma concentration profile of 20 mg/kg Biapenem as a function of time after administration to Swiss Webster mice.
Figure 4:
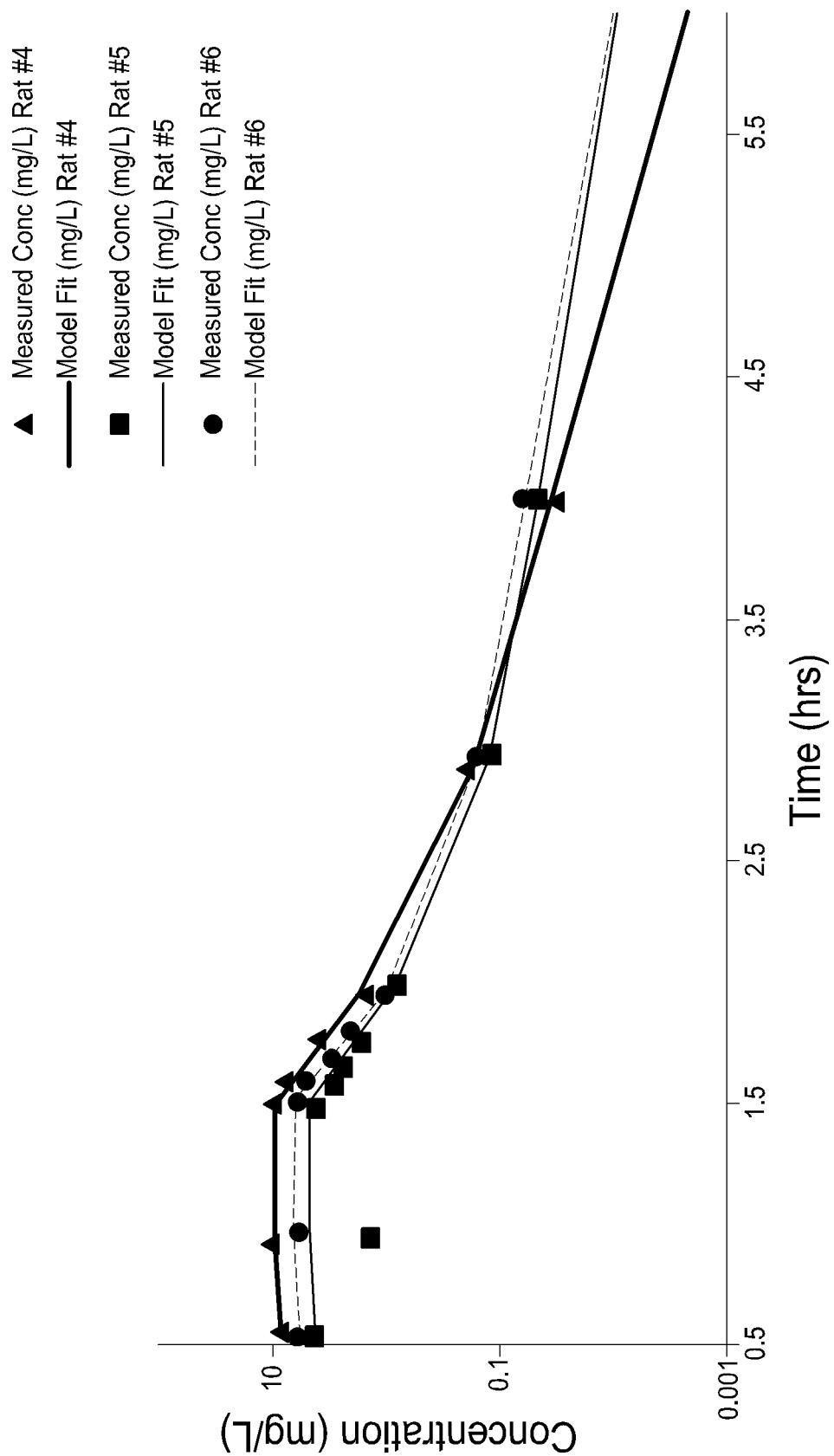
FIG. 4 is a graph depicting the plasma concentration profile of 20 mg/kg Compound I as a function of time after administration to Sprague-Dawley rats.
Figure 5:
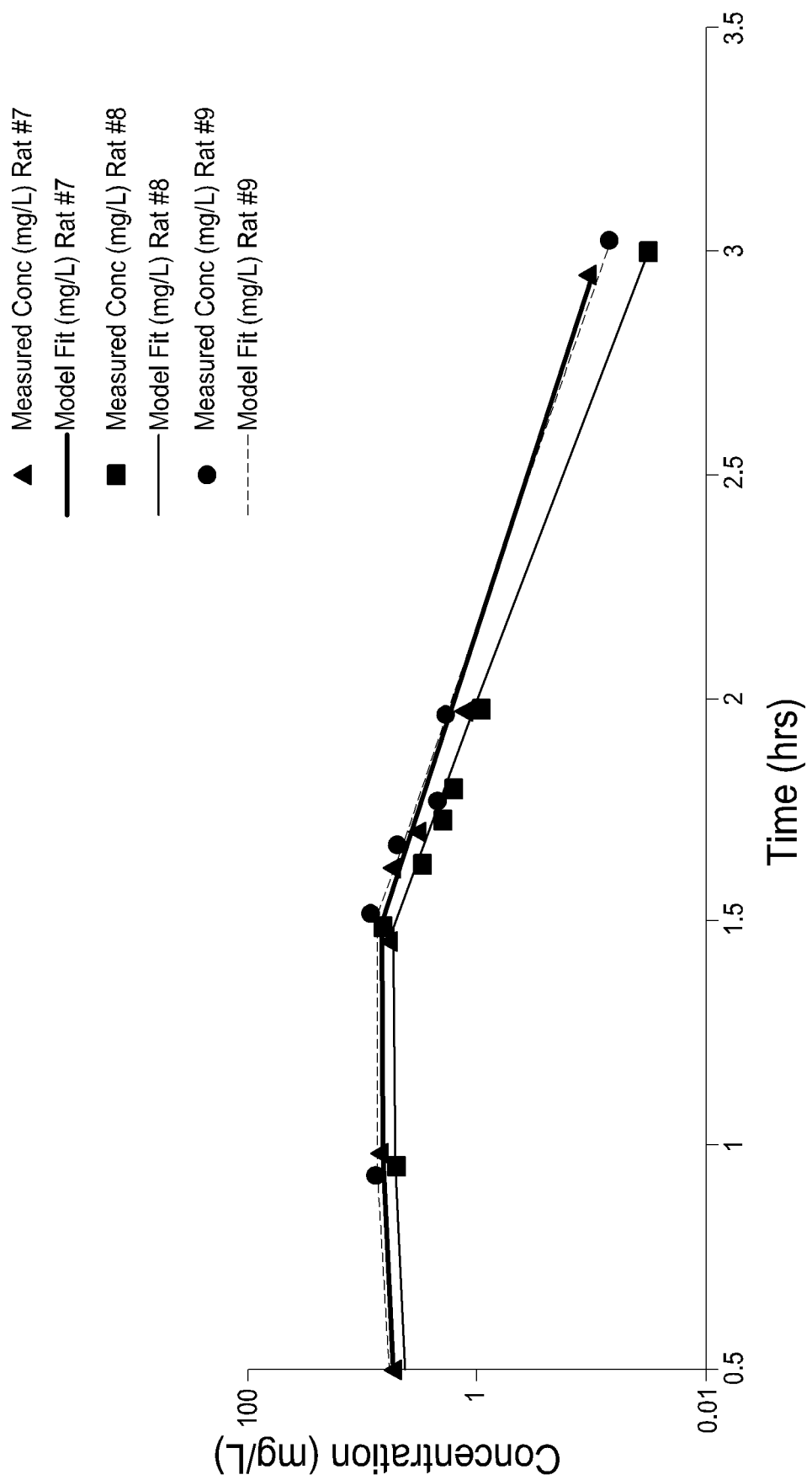
FIG. 5 is a graph depicting the plasma concentration profile of 20 mg/kg Biapenem in combination with 20 mg/kg Compound I as a function of time after administration to Sprague-Dawley rats.
Figure 6:
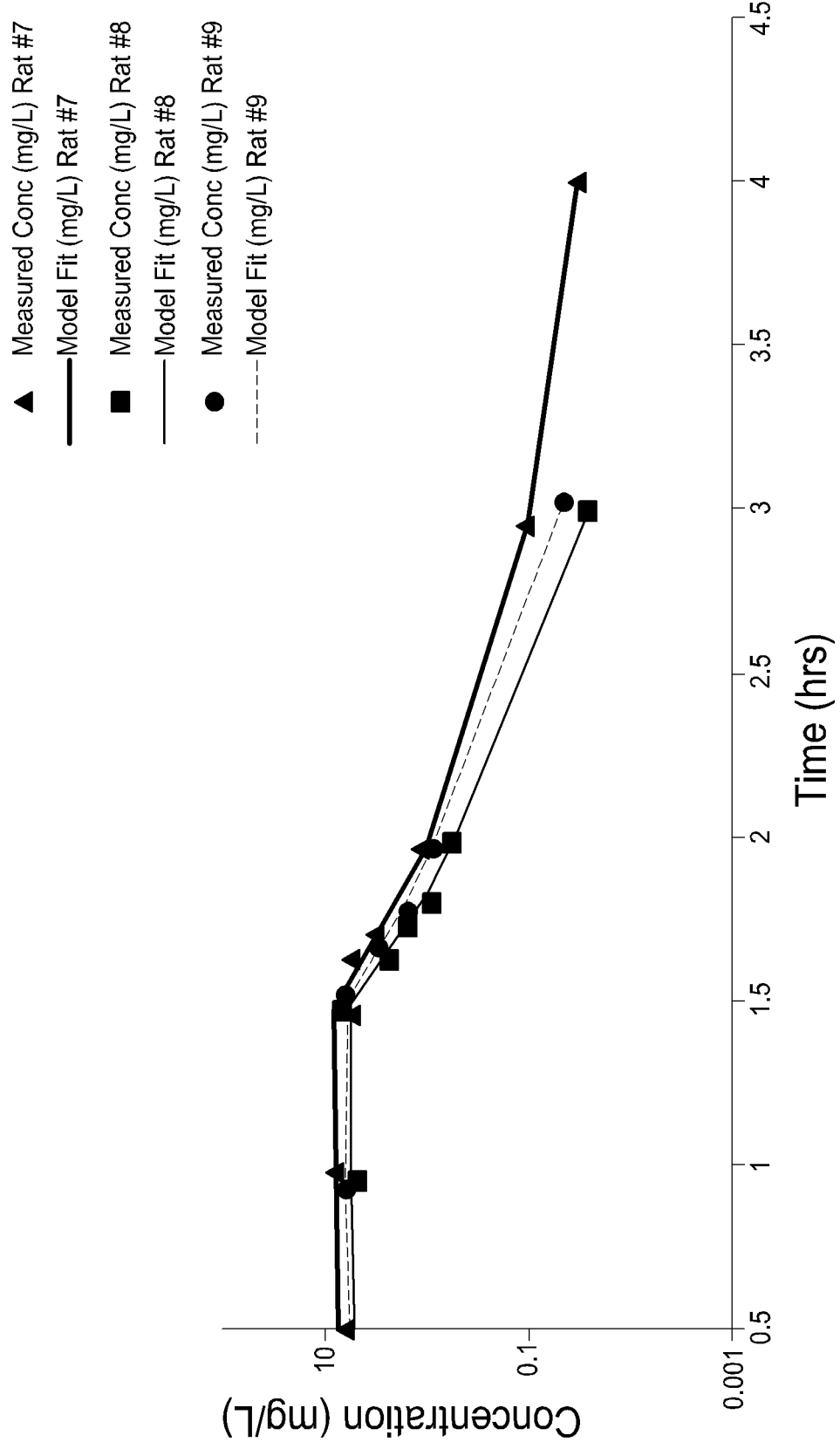
FIG. 6 is a graph depicting the plasma concentration profile of 20 mg/kg Compound I in combination with 20 mg/kg Biapenem as a function of time after administration to Sprague-Dawley rats.

The Plasma Pharmacokinetics of 25 mg/kg and 100 mg/kg of Biapenem after intraperitoneal dose of 25 or 100 mg/kg in Swiss Webster Mice are shown in FIG. 2 and Table 9.

TABLE 9

Plasma Pharmacokinetic Parameters of Biapenem in Swiss-Webster Mice

| Dose (mg/kg) | Cl (l/hr/kg) | AUC (hr*mg/kg) | Cmax (mg/l) | $T_{1/2}$ (h) |
|---|---|---|---|---|
| 25 | 1.6 | 15.56 | 31.2 | 0.17 |
| 100 | 0.96 | 103.55 | 286.0 | 0.21 |

The plasma standard curves of both studies were linear and used to determine the plasma concentrations. The plasma standard curve and concentrations are shown in Tables 10-13. The pharmacokinetic profile of biapenem was assessed in mice after single intraperitoneal doses of 25 and 100 mg/kg. Data indicates that Biapenem has a linear PK in Swiss-Webster mice over the dose range of 25 to 100 mg/kg.

TABLE 10

Plasma Standard Curve for Pharmacokinetics of 100 mg/kg of Biapenem

| Sample Name | Sample Type | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|---|
| mouse plasma blank | Unknown | 0 | N/A | 1.19 | 0.00E+00 | 46500 | No Peak |
| mouse plasma blank + IS | Unknown | 0 | N/A | 1.11 | 0.00E+00 | 268000 | No Peak |
| 0.01 ug/mL Biapenem in mouse plasma | Unknown | 5 | N/A | 0.955 | 1.91E-05 | 262000 | <0 |
| 0.02 ug/mL Biapenem in mouse plasma | Unknown | 155 | N/A | 1.3 | 5.74E-04 | 270000 | 0.0248 |
| 0.05 ug/mL Biapenem in mouse plasma | Standard | 315 | 0.05 | 1.17 | 1.15E-03 | 275000 | 0.0551 |
| 0.1 ug/mL Biapenem in mouse plasma | Standard | 578 | 0.1 | 1.18 | 2.17E-03 | 266000 | 0.109 |
| 0.2 ug/mL Biapenem in mouse plasma | Standard | 1190 | 0.2 | 1.17 | 4.33E-03 | 275000 | 0.224 |
| 0.5 ug/mL Biapenem in mouse plasma | Standard | 2960 | 0.5 | 1.17 | 1.11E-02 | 266000 | 0.582 |
| 1 ug/mL Biapenem in mouse plasma | Standard | 5910 | 1 | 1.17 | 2.18E-02 | 271000 | 1.15 |
| 2 ug/mL Biapenem in mouse plasma | Standard | 10900 | 2 | 1.17 | 4.02E-02 | 272000 | 2.13 |
| 5 ug/mL Biapenem in mouse plasma | Standard | 25600 | 5 | 1.19 | 9.85E-02 | 260000 | 5.28 |
| 10 ug/mL Biapenem in mouse plasma | Standard | 49800 | 10 | 1.18 | 1.90E-01 | 262000 | 10.3 |

TABLE 10-continued

Plasma Standard Curve for Pharmacokinetics of 100 mg/kg of Biapenem

| Sample Name | Sample Type | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|---|
| 20 ug/mL Biapenem in mouse plasma | Standard | 95400 | 20 | 1.17 | 3.66E−01 | 261000 | 20.5 |
| 50 ug/mL Biapenem in mouse plasma | Standard | 218000 | 50 | 1.15 | 8.29E−01 | 263000 | 50.7 |
| 100 ug/mL Biapenem in mouse plasma | Standard | 413000 | 100 | 1.17 | 1.47E+00 | 282000 | 110 |
| wash | Unknown | 5 | N/A | 1.19 | 2.76E−03 | 1810 | 0.141 |

TABLE 11

Plasma concentrations for Pharmacokinetics of 100 mg/kg of Biapenem

| Sample Name | Sample Type | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|---|
| mouse# 1.1 No dil. | Unknown | 692000 | N/A | 1.14 | 2.40E+00 | 288000 | No Intercept |
| mouse# 1.2 No dil. | Unknown | 3520 | N/A | 1.22 | 3.43E+00 | 1030 | No Intercept |
| mouse# 1.3 No dil. | Unknown | 705000 | N/A | 1.14 | 2.57E+00 | 274000 | No Intercept |
| mouse# 1.4 No dil. | Unknown | 297000 | N/A | 1.13 | 1.12E+00 | 264000 | 74.2 |
| mouse# 1.5 No dil. | Unknown | 645 | N/A | 1.15 | 2.38E−03 | 271000 | 0.120 |
| mouse# 1.6 No dil. | Unknown | 142000 | N/A | 1.14 | 5.30E−01 | 267000 | 30.5 |
| mouse# 1.7 No dil. | Unknown | 53100 | N/A | 1.14 | 2.04E−01 | 260000 | 11.1 |
| mouse# 1.8 No dil. | Unknown | 1070 | N/A | 1.15 | 4.16E−03 | 258000 | 0.214 |
| mouse# 1.9 No dil. | Unknown | 88 | N/A | 1.1 | 3.38E−04 | 259000 | 0.0123 |
| mouse# 1.10 No dil. | Unknown | 80 | N/A | 1.09 | 2.97E−04 | 269000 | 0.0102 |
| mouse# 2.1 No dil. | Unknown | 711000 | N/A | 1.15 | 2.67E+00 | 266000 | No Intercept |
| mouse# 2.2 No dil. | Unknown | 678000 | N/A | 1.14 | 2.54E+00 | 267000 | No Intercept |
| mouse# 2.3 No dil. | Unknown | 275000 | N/A | 1.14 | 1.06E+00 | 261000 | 68.4 |
| mouse# 2.4 No dil. | Unknown | 398000 | N/A | 1.14 | 1.49E+00 | 268000 | 113 |
| mouse# 2.5 No dil. | Unknown | 720 | N/A | 1.15 | 2.77E−03 | 260000 | 0.141 |
| mouse# 2.6 No dil. | Unknown | 115000 | N/A | 1.15 | 4.44E−01 | 259000 | 25.2 |
| mouse# 2.7 No dil. | Unknown | 525 | N/A | 1.12 | 2.05E−03 | 256000 | 0.103 |
| mouse# 2.8 No dil. | Unknown | 14900 | N/A | 1.14 | 5.42E−02 | 276000 | 2.88 |
| mouse# 2.9 No dil. | Unknown | 98 | N/A | 1.27 | 3.77E−04 | 259000 | 0.0144 |
| mouse# 2.10 No dil. | Unknown | 128 | N/A | 1.13 | 4.77E−04 | 268000 | 0.0197 |
| mouse# 3.1 No dil. | Unknown | 9190 | N/A | 1.13 | 3.35E−02 | 275000 | 1.77 |
| mouse# 3.2 No dil. | Unknown | 575000 | N/A | 1.15 | 2.18E+00 | 264000 | No Intercept |
| mouse# 3.3 No dil. | Unknown | 832000 | N/A | 1.14 | 3.10E+00 | 269000 | No Intercept |
| mouse# 3.4 No dil. | Unknown | 229000 | N/A | 1.15 | 8.78E−01 | 261000 | 54.4 |
| mouse# 3.5 No dil. | Unknown | 853 | N/A | 1.18 | 3.25E−03 | 263000 | 0.166 |
| mouse# 3.6 No dil. | Unknown | 98500 | N/A | 1.15 | 3.76E−01 | 262000 | 21.1 |
| mouse# 3.7 No dil. | Unknown | 510000 | N/A | 1.17 | 1.88E+00 | 272000 | No Intercept |
| mouse# 3.8 No dil. | Unknown | 5380 | N/A | 1.11 | 2.05E−02 | 263000 | 1.08 |
| mouse# 3.9 No dil. | Unknown | 85 | N/A | 1.07 | 3.17E−04 | 268000 | 0.0112 |
| mouse# 3.10 No dil. | Unknown | 118 | N/A | 1.14 | 4.51E−04 | 260000 | 0.0183 |

TABLE 12

Plasma Standard Curve for lactamase of 25 mg/kg of Biapenem

| Sample Name | Sample Type | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|---|
| mouse plasma blank | Unknown | 0 | N/A | 1.19 | 0.00E+00 | 46500 | No Peak |
| mouse plasma blank + IS | Unknown | 0 | N/A | 1.11 | 0.00E+00 | 268000 | No Peak |

TABLE 12-continued

Plasma Standard Curve for lactamase of 25 mg/kg of Biapenem

| Sample Name | Sample Type | Analyte Peak Area (counts) | Analyte Conc. (ug/mL) | Analyte Retention Time (min) | Area Ratio | IS Peak Area (counts) | Calc. Conc. (ug/mL) |
| --- | --- | --- | --- | --- | --- | --- | --- |
| 0.01 ug/mL Biapenem in mouse plasma | Unknown | 5 | N/A | 0.955 | 1.91E−05 | 262000 | <0 |
| 0.02 ug/mL Biapenem in mouse plasma | Unknown | 155 | N/A | 1.3 | 5.74E−04 | 270000 | 0.0248 |
| 0.05 ug/mL Biapenem in mouse plasma | Standard | 315 | 0.05 | 1.17 | 1.15E−03 | 275000 | 0.0551 |
| 0.1 ug/mL Biapenem in mouse plasma | Standard | 578 | 0.1 | 1.18 | 2.17E−03 | 266000 | 0.109 |
| 0.2 ug/mL Biapenem in mouse plasma | Standard | 1190 | 0.2 | 1.17 | 4.33E−03 | 275000 | 0.224 |
| 0.5 ug/mL Biapenem in mouse plasma | Standard | 2960 | 0.5 | 1.17 | 1.11E−02 | 266000 | 0.582 |
| 1 ug/mL Biapenem in mouse plasma | Standard | 5910 | 1 | 1.17 | 2.18E−02 | 271000 | 1.15 |
| 2 ug/mL Biapenem in mouse plasma | Standard | 10900 | 2 | 1.17 | 4.02E−02 | 272000 | 2.13 |
| 5 ug/mL Biapenem in mouse plasma | Standard | 25600 | 5 | 1.19 | 9.85E−02 | 260000 | 5.28 |
| 10 ug/mL Biapenem in mouse plasma | Standard | 49800 | 10 | 1.18 | 1.90E−01 | 262000 | 10.3 |
| 20 ug/mL Biapenem in mouse plasma | Standard | 95400 | 20 | 1.17 | 3.66E−01 | 261000 | 20.5 |
| 50 ug/mL Biapenem in mouse plasma | Standard | 218000 | 50 | 1.15 | 8.29E−01 | 263000 | 50.7 |
| 100 ug/mL Biapenem in mouse plasma | Standard | 413000 | 100 | 1.17 | 1.47E+00 | 282000 | 110 |
| wash | Unknown | 5 | N/A | 1.19 | 2.76E−03 | 1810 | 0.141 |

TABLE 13

Plasma concentrations for Pharmacokinetics of 25 mg/kg of Biapenem

| Sample Name | Sample Type | Analyte Peak Area (counts) | Analyte Conc. (ug/mL) | Analyte Retention Time (min) | Area Ratio | IS Peak Area (counts) | Calc. Conc. (ug/mL) |
| --- | --- | --- | --- | --- | --- | --- | --- |
| mouse# 1.1 No dil. | Unknown | 385 | N/A | 1.11 | 1.47E−03 | 262000 | 0.0723 |
| mouse# 1.2 No dil. | Unknown | 88400 | N/A | 1.18 | 3.42E−01 | 259000 | 19.1 |
| mouse# 1.3 No dil. | Unknown | 89700 | N/A | 1.17 | 3.59E−01 | 250000 | 20.0 |
| mouse# 1.4 No dil. | Unknown | 71600 | N/A | 1.16 | 2.76E−01 | 259000 | 15.2 |
| mouse# 1.5 No dil. | Unknown | 38900 | N/A | 1.15 | 1.51E−01 | 257000 | 8.18 |
| mouse# 1.6 No dil. | Unknown | 478 | N/A | 1.13 | 1.92E−03 | 249000 | 0.0959 |
| mouse# 1.7 No dil. | Unknown | 7710 | N/A | 1.15 | 3.01E−02 | 256000 | 1.59 |
| mouse# 1.8 No dil. | Unknown | 505 | N/A | 1.27 | 2.04E−03 | 248000 | 0.102 |
| mouse# 1.9 No dil. | Unknown | 0 | N/A | 1.13 | 0.00E+00 | 252000 | No Peak |
| mouse# 1.10 No dil. | Unknown | 0 | N/A | 1.01 | 0.00E+00 | 252000 | No Peak |
| mouse# 2.1 No dil. | Unknown | 96200 | N/A | 1.16 | 3.85E−01 | 250000 | 21.6 |
| mouse# 2.2 No dil. | Unknown | 71400 | N/A | 1.15 | 2.74E−01 | 261000 | 15.1 |
| mouse# 2.3 No dil. | Unknown | 221000 | N/A | 1.16 | 8.44E−01 | 262000 | 51.8 |
| mouse# 2.4 No dil. | Unknown | 63100 | N/A | 1.15 | 2.42E−01 | 260000 | 13.3 |
| mouse# 2.5 No dil. | Unknown | 645 | N/A | 1.14 | 2.64E−03 | 245000 | 0.268 |
| mouse# 2.6 No dil. | Unknown | 29500 | N/A | 1.16 | 1.13E−01 | 261000 | 6.07 |
| mouse# 2.7 No dil. | Unknown | 230 | N/A | 1.23 | 9.28E−04 | 248000 | 0.0436 |
| mouse# 2.8 No dil. | Unknown | 348 | N/A | 1.16 | 1.34E−03 | 259000 | 0.0656 |
| mouse# 2.9 No dil. | Unknown | 0 | N/A | 1.1 | 0.00E+00 | 251000 | No Peak |
| mouse# 2.10 No dil. | Unknown | 0 | N/A | 1.07 | 0.00E+00 | 265000 | No Peak |
| mouse# 3.1 No dil. | Unknown | 111000 | N/A | 1.14 | 4.28E−01 | 259000 | 24.2 |
| mouse# 3.2 No dil. | Unknown | 120000 | N/A | 1.16 | 4.72E−01 | 254000 | 26.9 |
| mouse# 3.3 No dil. | Unknown | 99400 | N/A | 1.14 | 3.86E−01 | 257000 | 21.7 |
| mouse# 3.4 No dil. | Unknown | 87500 | N/A | 1.16 | 3.38E−01 | 259000 | 18.8 |
| mouse# 3.5 No dil. | Unknown | 62800 | N/A | 1.15 | 2.41E−01 | 261000 | 13.2 |
| mouse# 3.6 No dil. | Unknown | 32100 | N/A | 1.16 | 1.25E−01 | 255000 | 6.75 |
| mouse# 3.7 No dil. | Unknown | 19400 | N/A | 1.17 | 7.37E−02 | 263000 | 3.93 |
| mouse# 3.8 No dil. | Unknown | 575 | N/A | 1.13 | 2.28E−03 | 252000 | 0.115 |
| mouse# 3.9 No dil. | Unknown | 0 | N/A | 0.999 | 0.00E+00 | 259000 | No Peak |
| mouse# 3.10 No dil. | Unknown | 203 | N/A | 1.17 | 7.63E−04 | 265000 | 0.0348 |

Example 3

Example 3 provides a summary of the pharmacokinetic studies of Compound I alone or in combination with Biapenem following a single intravenous infusion dose in Sprague-Dawley rats. The pharmacokinetics of 20 mg/kg of Compound I, 20 mg/kg of Biapenem, and 20 mg/kg of Compound I in combination with 20 mg/kg of Biapenem after a 1.5 hour intravenous infusion were discussed.

Materials and Methods

Biapenem power was purchased from Hisun Pharmaceuticals. Compound I was prepared using the method described in the U.S. Publication 2012/0040932 A1. 20 mg of biapenem was dissolved in 0.1 M $NaH_2PO_4$ for a basic stock solution. 100 mg of Compound I was dissolved in 30% 1N NaOH to ~pH 5.0. For animal studies, these stock solutions were further diluted in 0.9% saline to the appropriate concentration.

The specifications for animals used on this study were as follows:
Species: Rat
Strain: Sprague-Dawley
Gender: Male
Source: Charles River (Hollister, Calif.)
Number of Animals: 3 per study
Body Weight Range: 230-280 g at the start of the study Upon receipt, animals were housed individually per cage in a room with a controlled environment and were acclimated to laboratory conditions for at least 24 hours prior to the start of dosing. Animals were provided food and water ad libitum. The health status of the animals was determined during the acclimation period and unhealthy animals were not placed on study. Each animal was identified by marking their tails with indelible ink and each cage was identified by animal, group, and study number.

After acclimation, rats (n=3) were administered single 20 mg/kg intravenous infusion doses of Compound I or Biapenem alone or in combination. Doses were infused over 1.5 hours via an indwelling femoral vein cannula. Plasma (~0.3 mL) samples were collected from each rat at designated time points up to 24 hours. The time points are shown in section 2.9. Blood samples were centrifuged within 5 min of collection at 12000 g for 5 min to obtain plasma. The plasma samples were stored on −80° C. until analyzed.

Compound I standard curves were prepared in rat plasma from 0.1 to 100 μg/mL. 50 μl aliquots of sample were placed in 1.5 mL microcentrifuge tubes. 20 μl of Compound II (10 μg/mL) was added as internal standard to each sample or standard. 20 μl of 30% trichloroacetic acid was then added to each sample or standard. The samples were mixed using a vortex mixer centrifuged for 10 min at 15,000 RPM using a tabletop centrifuge. The supernatant (approx. 120 μl) was removed and added to 100 μl of water in a 96-well plate. The samples were mixed again using a vortex mixer. 10 μl of each sample was injected onto an HPLC-MS for quantification.

The HPLC-MS conditions for Compound I analysis are as follows:
Column: Phenomenex Fusion-RP or equivalent reversed-phase column, 5 um, 50×2 mm.
Flow rate: 0.6 mL/min.
Mobile phase A: 0.1% formic acid in water.
Mobile phase B: 0.1% formic acid in acetonitrile.
Gradient: 5-60% B in 1.5 min.
Mass spectrometer: Negative ion mode with electrospray ionization.
MS/MS: Compound I-Q1-m/e=296, Q3-m/e=234.
Compound II-Q1-m/e=331, Q3-m/e=201.

Biapenem standard curves were prepared in 50% plasma-50% 1M MOPS buffer, pH=7.4 from 1 to 250 ug/mL. 20 uL of sample or standard was added into a 96-well deep well plate. Then 500 uL of 10% water-45% methanol-45% acetonitrile containing 2 ug/mL of meropenem was used as an internal standard. The plate was vortexed for 15 min. at 3,000 RPM. 50 uL of supernatant was removed and added 300 uL of water. 10 uL of samples were injected onto an HPLC-MS system for quantification.

The HPLC-MS conditions for Biaphenem analysis are as follows:
Column: Supelco Discovery HS F5 or equivalent pentafluorophenyl column, 5 um, 50×2.1 mm.
Flow rate: 0.6 mL/min.
Mobile phase A: 0.1% formic acid in water.
Mobile phase B: 0.1% formic acid in acetonitrile.
Gradient: 5-70% B in 1.9 min.
Mass spectrometer: Positive ion mode with electrospray ionization.
MS/MS: Biapenem-Q1-m/e=350.8, Q3-m/e=110.1.
meropenem-Q1-m/e=384.1, Q3-m/e=141.1

Plasma concentrations were fit using a two compartment IV infusion model (WinNonlinVersion 5.3, Pharsight Corp, Mountain View, Calif.).

The study groups, dose and dose routes for the three pharmacokinetic studies are shown in the table below:

| Compounds | Dose (mg/kg) | Plasma Collection Time Points (hr) | Number of Animal per Timepoint | Length of Infusion (hr) | Route of Administration |
|---|---|---|---|---|---|
| Compound I + Biapenem | 20 + 20 | 0.5, 1, 1.5, 1.58, 1.67, 1.75, 2, 3, 4, 6, 24 | 3 | 1.5 | Intravenous Infusion |
| Compound I | 20 | | | | |
| Biapenem | 0 + 20 | | | | |

The Sprague-Dawley rats plasma pharmacokinetics of 20 mg/kg of Compound I and Biapenem alone or in combination are shown in FIGS. 3-6 and Table 14.

TABLE 14

Pharmacokinetics of Biapenem and Compound I Administered Alone or in Combination in Rats

| | AUC (mg*h/L) | Cl (L/hr/kg) | Half-Life (hr) |
|---|---|---|---|
| Biapenem PK | | | |
| Biapenem (alone) | 8.95 ± 0.89 | 2.29 ± 0.24 | 0.21 ± 0.01 |
| Biapenem (with Compound I) | 10.07 ± 1.13 | 2.03 ± 0.22 | 0.22 ± 0.01 |

TABLE 14-continued

Pharmacokinetics of Biapenem and Compound I Administered Alone or in Combination in Rats

|  | AUC (mg*h/L) | Cl (L/hr/kg) | Half-Life (hr) |
|---|---|---|---|
| Compound I PK |  |  |  |
| Compound I (alone) | 10.98 ± 0.86 | 1.98 ± 0.12 | 0.72 ± 0.15 |
| Compound I (with Biapenem) | 10.44 ± 1.15 | 1.95 ± 0.21 | 0.39 ± 0.11 |

The plasma standard curves of all three studies were linear and used to determine the plasma concentrations. The plasma standard curve and concentrations of three studies are shown in Tables 15-22. The pharmacokinetic profiles of Compound I and Biapenem alone or in combination were assessed in rats after single intravenous infusion. Data shows that the plasma pharmacokinetic parameters for biapenem and Compound I in rats are similar to each other and are unchanged when they were administered alone or in combination.

TABLE 15

Plasma Standard Curve of 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| rat r.p.. blank + IS | 0 | N/A | 0 | 0.00E+00 | 975000 | No Peak |
| 0.01 ug/mL Biapenem & Compound I in rat r.p.. | 230 | 0.01 | 0.48 | 2.36E−04 | 974000 | 0.00754 |
| 0.02 ug/mL Biapenem & Compound I in rat r.p.. | 523 | 0.02 | 0.494 | 5.24E−04 | 998000 | 0.0209 |
| 0.05 ug/mL Biapenem & Compound I in rat r.p.. | 1250 | 0.05 | 0.49 | 1.28E−03 | 978000 | 0.0561 |
| 0.1 ug/mL Biapenem & Compound I in rat r.p.. | 2370 | 0.1 | 0.49 | 2.51E−03 | 946000 | 0.114 |
| 0.2 ug/mL Biapenem & Compound I in rat r.p.. | 4230 | 0.2 | 0.49 | 4.43E−03 | 955000 | 0.204 |
| 0.5 ug/mL Biapenem & Compound I in rat r.p.. | 10500 | 0.5 | 0.485 | 1.10E−02 | 957000 | 0.518 |
| 1 ug/mL Biapenem & Compound I in rat r.p.. | 21200 | 1 | 0.491 | 2.16E−02 | 978000 | 1.04 |
| 2 ug/mL Biapenem & Compound I in rat r.p.. | 38900 | 2 | 0.486 | 4.25E−02 | 915000 | 2.12 |
| 5 ug/mL Biapenem & Compound I in rat r.p.. | 77900 | 5 | 0.486 | 8.56E−02 | 910000 | 4.72 |
| 10 ug/mL Biapenem & Compound I in rat r.p.. | 132000 | 10 | 0.49 | 1.42E−01 | 936000 | 9.78 |
| 20 ug/mL Biapenem & Compound I in rat r.p.. | 219000 | N/A | 0.487 | 2.43E−01 | 901000 | No Intercept |
| 50 ug/mL Biapenem & Compound I in rat r.p.. | 410000 | N/A | 0.485 | 4.44E−01 | 923000 | No Intercept |
| 100 ug/mL Biapenem & Compound I in rat r.p.. | 617000 | N/A | 0.492 | 6.79E−01 | 909000 | No Intercept |

TABLE 16

Plasma Concentrations of 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| r.p. # 1.1 (Biapenem 20 mg/kg) | 84000 | N/A | 0.481 | 9.70E−02 | 866000 | 5.53 |
| r.p. # 1.2 (Biapenem 20 mg/kg) | 76700 | N/A | 0.496 | 8.94E−02 | 858000 | 4.99 |
| r.p. # 1.3 (Biapenem 20 mg/kg) | 106000 | N/A | 0.49 | 1.28E−01 | 826000 | 8.18 |
| r.p. # 1.4 (Biapenem 20 mg/kg) | 91000 | N/A | 0.482 | 1.08E−01 | 845000 | 6.4 |
| r.p. # 1.5 (Biapenem 20 mg/kg) | 64100 | N/A | 0.486 | 7.60E−02 | 843000 | 4.09 |
| r.p. # 1.6 (Biapenem 20 mg/kg) | 46000 | N/A | 0.485 | 5.56E−02 | 828000 | 2.85 |
| r.p. # 1.7 (Biapenem 20 mg/kg) | 24800 | N/A | 0.485 | 3.06E−02 | 813000 | 1.49 |
| r.p. # 1.8 (Biapenem 20 mg/kg) | 2140 | N/A | 0.49 | 2.60E−03 | 824000 | 0.118 |
| r.p. # 1.9 (Biapenem 20 mg/kg) | 95 | N/A | 0.495 | 1.14E−04 | 835000 | 0.00185 |
| r.p. # 1.10 (Biapenem 20 mg/kg) | 20 | N/A | 0.475 | 2.42E−05 | 826000 | <0 |
| r.p. # 1.10 (Biapenem 20 mg/kg) | 10 | N/A | 0.49 | 1.23E−05 | 801000 | <0 |
| r.p. # 2.1 (Biapenem 20 mg/kg) | 73700 | N/A | 0.482 | 9.07E−02 | 812000 | 5.08 |
| No Sample | N/A | N/A | N/A | N/A | N/A | N/A |
| r.p. # 2.3 (Biapenem 20 mg/kg) | 83900 | N/A | 0.482 | 1.03E−01 | 813000 | 6.01 |
| r.p. # 2.4 (Biapenem 20 mg/kg) | 59900 | N/A | 0.486 | 7.55E−02 | 794000 | 4.06 |
| r.p. # 2.5 (Biapenem 20 mg/kg) | 34300 | N/A | 0.486 | 4.31E−02 | 796000 | 2.15 |

TABLE 16-continued

Plasma Concentrations of 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| r.p. # 2.6 (Biapenem 20 mg/kg) | 12500 | N/A | 0.481 | 1.53E−02 | 820000 | 0.725 |
| r.p. # 2.7 (Biapenem 20 mg/kg) | 14900 | N/A | 0.49 | 1.84E−02 | 808000 | 0.878 |
| r.p. # 2.8 (Biapenem 20 mg/kg) | 1570 | N/A | 0.491 | 2.02E−03 | 778000 | 0.0906 |
| r.p. # 2.9 (Biapenem 20 mg/kg) | 93 | N/A | 0.474 | 1.17E−04 | 788000 | 0.00201 |
| r.p. # 2.10 (Biapenem 20 mg/kg) | 418 | N/A | 0.488 | 5.29E−04 | 790000 | 0.0212 |
| r.p. # 2.10 (Biapenem 20 mg/kg) | 0 | N/A | 0 | 0.00E+00 | 770000 | No Peak |
| r.p. # 3.1 (Biapenem 20 mg/kg) | 59800 | N/A | 0.49 | 7.91E−02 | 757000 | 4.29 |
| r.p. # 3.2 (Biapenem 20 mg/kg) | 53500 | N/A | 0.491 | 6.95E−02 | 769000 | 3.68 |
| r.p. # 3.3 (Biapenem 20 mg/kg) | 76800 | N/A | 0.487 | 1.02E−01 | 752000 | 5.92 |
| r.p. # 3.4 (Biapenem 20 mg/kg) | 61400 | N/A | 0.489 | 7.65E−02 | 802000 | 4.12 |
| r.p. # 3.5 (Biapenem 20 mg/kg) | 31100 | N/A | 0.494 | 4.15E−02 | 749000 | 2.07 |
| r.p. # 3.6 (Biapenem 20 mg/kg) | 24500 | N/A | 0.49 | 3.30E−02 | 742000 | 1.62 |
| r.p. # 3.7 (Biapenem 20 mg/kg) | 13200 | N/A | 0.486 | 1.73E−02 | 760000 | 0.824 |
| r.p. # 3.8 (Biapenem 20 mg/kg) | 743 | N/A | 0.489 | 9.49E−04 | 783000 | 0.0407 |
| r.p. # 3.9 (Biapenem 20 mg/kg) | 185 | N/A | 0.493 | 2.49E−04 | 743000 | 0.00814 |
| r.p. # 3.10 (Biapenem 20 mg/kg) | 23 | N/A | 0.452 | 2.93E−05 | 769000 | <0 |

TABLE 17

Plasma Standard Curve of 20 mg/kg of Compound I

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| r.k.h. blank | 0 | N/A | 0 | 0.00E+00 | 8 | No Peak |
| rat r.p.. blank + IS | 0 | N/A | 0 | 0.00E+00 | 134000 | No Peak |
| 0.01 ug/mL Biapenem & Compound I in rat r.p.. | 711 | N/A | 2.13 | 5.01E−03 | 142000 | 0.0193 |
| 0.02 ug/mL Biapenem & Compound I in rat r.p.. | 851 | 0.02 | 2.14 | 5.37E−03 | 158000 | 0.0217 |
| 0.05 ug/mL Biapenem & Compound I in rat r.p.. | 1600 | 0.05 | 2.13 | 9.84E−03 | 163000 | 0.0509 |
| 0.1 ug/mL Biapenem & Compound I in rat r.p.. | 2950 | 0.1 | 2.15 | 1.67E−02 | 177000 | 0.0959 |
| 0.2 ug/mL Biapenem & Compound I in rat r.p.. | 6460 | 0.2 | 2.14 | 3.43E−02 | 188000 | 0.211 |
| 0.5 ug/mL Biapenem & Compound I in rat r.p.. | 14700 | 0.5 | 2.14 | 7.72E−02 | 191000 | 0.493 |
| 1 ug/mL Biapenem & Compound I in rat r.p.. | 32900 | 1 | 2.14 | 1.69E−01 | 195000 | 1.09 |
| 2 ug/mL Biapenem & Compound I in rat r.p.. | 66000 | 2 | 2.14 | 3.15E−01 | 209000 | 2.07 |
| 5 ug/mL Biapenem & Compound I in rat r.p.. | 165000 | 5 | 2.14 | 7.94E−01 | 208000 | 5.29 |
| 10 ug/mL Biapenem & Compound I in rat r.p.. | 340000 | 10 | 2.14 | 1.59E+00 | 214000 | 10.8 |
| 20 ug/mL Biapenem & Compound I in rat r.p.. | 647000 | 20 | 2.14 | 2.99E+00 | 216000 | 21.2 |
| 50 ug/mL Biapenem & Compound I in rat r.p.. | 1450000 | 50 | 2.14 | 6.47E+00 | 224000 | 52.5 |
| 100 ug/mL Biapenem & Compound I in rat r.p.. | 2510000 | 100 | 2.14 | 1.05E+01 | 240000 | No Intercept |
| wash | 28500 | N/A | 2.13 | 9.49E+02 | 30 | No Intercept |

TABLE 18

Plasma Concentrations of 20 mg/kg of Compound I

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| r.p. # 4.1 (Compound I 20 mg/kg) | 344000 | N/A | 2.14 | 1.17E+00 | 294000 | 7.88 |
| r.p. # 4.2 (Compound I 20 mg/kg) | 408000 | N/A | 2.14 | 1.55E+00 | 263000 | 10.6 |
| r.p. # 4.3 (Compound I 20 mg/kg) | 417000 | N/A | 2.14 | 1.44E+00 | 289000 | 9.80 |
| r.p. # 4.4 (Compound I 20 mg/kg) | 317000 | N/A | 2.14 | 1.12E+00 | 283000 | 7.51 |
| r.p. # 4.6 (Compound I 20 mg/kg) | 135000 | N/A | 2.14 | 4.69E-01 | 288000 | 3.09 |
| r.p. # 4.5 (Compound I 20 mg/kg) | 188000 | N/A | 2.14 | 6.47E-01 | 290000 | 4.29 |
| r.p. # 4.7 (Compound I 20 mg/kg) | 68200 | N/A | 2.14 | 2.30E-01 | 297000 | 1.50 |
| r.p. # 4.8 (Compound I 20 mg/kg) | 9100 | N/A | 2.14 | 3.00E-02 | 303000 | 0.183 |
| r.p. # 4.9 (Compound I 20 mg/kg) | 2380 | N/A | 2.14 | 7.50E-03 | 317000 | 0.0356 |
| r.p. # 4.10 (Compound I 20 mg/kg) | 3060 | N/A | 2.15 | 9.67E-03 | 316000 | 0.0498 |
| r.p. # 4.10 (Compound I 20 mg/kg) | 372 | N/A | 2.12 | 1.19E-03 | 314000 | <0 |
| r.p. # 5.1 (Compound I 20 mg/kg) | 206000 | N/A | 2.15 | 6.70E-01 | 307000 | 4.45 |
| r.p. # 5.2 (Compound I 20 mg/kg) | 72100 | N/A | 2.14 | 2.24E-01 | 321000 | 1.46 |
| r.p. # 5.3 (Compound I 20 mg/kg) | 222000 | N/A | 2.15 | 6.83E-01 | 325000 | 4.53 |
| r.p. # 5.4 (Compound I 20 mg/kg) | 159000 | N/A | 2.14 | 4.79E-01 | 333000 | 3.16 |
| r.p. # 5.5 (Compound I 20 mg/kg) | 130000 | N/A | 2.14 | 3.96E-01 | 328000 | 2.61 |
| r.p. # 5.6 (Compound I 20 mg/kg) | 92400 | N/A | 2.14 | 2.81E-01 | 329000 | 1.84 |
| r.p. # 5.7 (Compound I 20 mg/kg) | 46000 | N/A | 2.14 | 1.38E-01 | 332000 | 0.896 |
| r.p. # 5.8 (Compound I 20 mg/kg) | 7290 | N/A | 2.14 | 2.08E-02 | 351000 | 0.122 |
| r.p. # 5.9 (Compound I 20 mg/kg) | 3130 | N/A | 2.15 | 9.21E-03 | 340000 | 0.0468 |
| r.p. # 5.10 (Compound I 20 mg/kg) | 3300 | N/A | 2.15 | 9.56E-03 | 345000 | 0.0491 |
| r.p. # 5.10 (Compound I 20 mg/kg) | 233 | N/A | 2.15 | 6.56E-04 | 354000 | <0 |
| r.p. # 6.1 (Compound I 20 mg/kg) | 346000 | N/A | 2.15 | 9.79E-01 | 354000 | 6.55 |
| r.p. # 6.2 (Compound I 20 mg/kg) | 289000 | N/A | 2.14 | 8.17E-01 | 354000 | 5.44 |
| r.p. # 6.3 (Compound I 20 mg/kg) | 294000 | N/A | 2.15 | 8.38E-01 | 350000 | 5.59 |
| r.p. # 6.4 (Compound I 20 mg/kg) | 280000 | N/A | 2.14 | 7.87E-01 | 355000 | 5.24 |
| r.p. # 6.5 (Compound I 20 mg/kg) | 159000 | N/A | 2.15 | 4.44E-01 | 359000 | 2.92 |
| r.p. # 6.6 (Compound I 20 mg/kg) | 120000 | N/A | 2.15 | 3.19E-01 | 377000 | 2.09 |
| r.p. # 6.7 (Compound I 20 mg/kg) | 57000 | N/A | 2.14 | 1.48E-01 | 385000 | 0.960 |
| r.p. # 6.8 (Compound I 20 mg/kg) | 9680 | N/A | 2.14 | 2.66E-02 | 363000 | 0.161 |
| r.p. # 6.9 (Compound I 20 mg/kg) | 4200 | N/A | 2.14 | 1.11E-02 | 380000 | 0.0589 |
| r.p. # 6.10 (Compound I 20 mg/kg) | 3930 | N/A | 2.15 | 1.07E-02 | 366000 | 0.0567 |
| r.p. # 6.10 (Compound I 20 mg/kg) | 274 | N/A | 2.15 | 7.19E-04 | 381000 | <0 |

TABLE 19

Compound I Plasma Standard Curve of 20 mg/kg of Compound I in Combination with 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| r.k.h. blank | 0 | N/A | 0 | 0.00E+00 | 8 | No Peak |
| rat r.p.. blank + IS | 0 | N/A | 0 | 0.00E+00 | 134000 | No Peak |
| 0.01 ug/mL Biapenem & Compound I in rat r.p.. | 711 | N/A | 2.13 | 5.01E-03 | 142000 | 0.0193 |
| 0.02 ug/mL Biapenem & Compound I in rat r.p.. | 851 | 0.02 | 2.14 | 5.37E-03 | 158000 | 0.0217 |
| 0.05 ug/mL Biapenem & Compound I in rat r.p.. | 1600 | 0.05 | 2.13 | 9.84E-03 | 163000 | 0.0509 |
| 0.1 ug/mL Biapenem & Compound I in rat r.p.. | 2950 | 0.1 | 2.15 | 1.67E-02 | 177000 | 0.0959 |
| 0.2 ug/mL Biapenem & Compound I in rat r.p.. | 6460 | 0.2 | 2.14 | 3.43E-02 | 188000 | 0.211 |
| 0.5 ug/mL Biapenem & Compound I in rat r.p.. | 14700 | 0.5 | 2.14 | 7.72E-02 | 191000 | 0.493 |
| 1 ug/mL Biapenem & Compound I in rat r.p.. | 32900 | 1 | 2.14 | 1.69E-01 | 195000 | 1.09 |
| 2 ug/mL Biapenem & Compound I in rat r.p.. | 66000 | 2 | 2.14 | 3.15E-01 | 209000 | 2.07 |
| 5 ug/mL Biapenem & Compound I in rat r.p.. | 165000 | 5 | 2.14 | 7.94E-01 | 208000 | 5.29 |
| 10 ug/mL Biapenem & Compound I in rat r.p.. | 340000 | 10 | 2.14 | 1.59E+00 | 214000 | 10.8 |
| 20 ug/mL Biapenem & Compound I in rat r.p.. | 647000 | 20 | 2.14 | 2.99E+00 | 216000 | 21.2 |

TABLE 19-continued

Compound I Plasma Standard Curve of 20 mg/kg of Compound I in Combination with 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| 50 ug/mL Biapenem & Compound I in rat r.p.. | 1450000 | 50 | 2.14 | 6.47E+00 | 224000 | 52.5 |
| 100 ug/mL Biapenem & Compound I in rat r.p.. | 2510000 | 100 | 2.14 | 1.05E+01 | 240000 | No Intercept |
| wash | 28500 | N/A | 2.13 | 9.49E+02 | 30 | No Intercept |

TABLE 20

Compound I Plasma Concentrations of 20 mg/kg of Compound I in Combination with 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| r.p. # 7.1 (Biapenem & Compound I 20 mg/kg) | 355000 | N/A | 2.15 | 8.25E-01 | 430000 | 5.50 |
| r.p. # 7.2 (Biapenem & Compound I 20 mg/kg) | 411000 | N/A | 2.14 | 1.08E+00 | 381000 | 7.24 |
| r.p. # 7.3 (Biapenem & Compound I 20 mg/kg) | 321000 | N/A | 2.14 | 8.18E-01 | 392000 | 5.45 |
| r.p. # 7.4 (Biapenem & Compound I 20 mg/kg) | 339000 | N/A | 2.15 | 8.46E-01 | 401000 | 5.64 |
| r.p. # 7.5 (Biapenem & Compound I 20 mg/kg) | 185000 | N/A | 2.14 | 4.55E-01 | 406000 | 3.00 |
| r.p. # 7.6 (Biapenem & Compound I 20 mg/kg) | 117000 | N/A | 2.14 | 2.95E-01 | 398000 | 1.93 |
| r.p. # 7.7 (Biapenem & Compound I 20 mg/kg) | 64300 | N/A | 2.14 | 1.63E-01 | 394000 | 1.06 |
| r.p. # 7.8 (Biapenem & Compound I 20 mg/kg) | 6860 | N/A | 2.14 | 1.72E-02 | 398000 | 0.0994 |
| r.p. # 7.9 (Biapenem & Compound I 20 mg/kg) | 2890 | N/A | 2.14 | 7.13E-03 | 406000 | 0.0332 |
| r.p. # 7.10 (Biapenem & Compound I 20 mg/kg) | 7600 | N/A | 2.15 | 1.88E-02 | 405000 | 0.109 |
| r.p. # 7.10 (Biapenem & Compound I 20 mg/kg) | 402 | N/A | 2.14 | 9.61E-04 | 418000 | <0 |
| r.p. # 8.1 (Biapenem & Compound I 20 mg/kg) | 354000 | N/A | 2.14 | 8.47E-01 | 417000 | 5.65 |
| r.p. # 8.2 (Biapenem & Compound I 20 mg/kg) | 317000 | N/A | 2.14 | 7.32E-01 | 432000 | 4.87 |
| r.p. # 8.3 (Biapenem & Compound I 20 mg/kg) | 415000 | N/A | 2.14 | 9.59E-01 | 433000 | 6.41 |
| r.p. # 8.4 (Biapenem & Compound I 20 mg/kg) | 159000 | N/A | 2.14 | 3.86E-01 | 411000 | 2.54 |
| r.p. # 8.5 (Biapenem & Compound I 20 mg/kg) | 106000 | N/A | 2.14 | 2.54E-01 | 417000 | 1.66 |
| r.p. # 8.6 (Biapenem & Compound I 20 mg/kg) | 60800 | N/A | 2.14 | 1.42E-01 | 428000 | 0.920 |
| r.p. # 8.7 (Biapenem & Compound I 20 mg/kg) | 37900 | N/A | 2.14 | 9.08E-02 | 418000 | 0.582 |
| r.p. # 8.8 (Biapenem & Compound I 20 mg/kg) | 2550 | N/A | 2.14 | 5.95E-03 | 429000 | 0.0254 |
| r.p. # 8.9 (Biapenem & Compound I 20 mg/kg) | 3030 | N/A | 2.13 | 6.95E-03 | 436000 | 0.0320 |
| r.p. # 8.10 (Biapenem & Compound I 20 mg/kg) | 5140 | N/A | 2.13 | 1.22E-02 | 421000 | 0.0664 |
| r.p. # 8.10 (Biapenem & Compound I 20 mg/kg) | 180 | N/A | 2.14 | 4.23E-04 | 426000 | <0 |
| r.p. # 9.1 (Biapenem & Compound I 20 mg/kg) | 286000 | N/A | 2.14 | 6.58E-01 | 435000 | 4.36 |
| r.p. # 9.2 (Biapenem & Compound I 20 mg/kg) | 431000 | N/A | 2.14 | 9.42E-01 | 458000 | 6.30 |
| r.p. # 9.3 (Biapenem & Compound I 20 mg/kg) | 465000 | N/A | 2.14 | 1.05E+00 | 441000 | 7.07 |
| No Sample | N/A | N/A | N/A | N/A | N/A | N/A |
| r.p. # 9.5 (Biapenem & Compound I 20 mg/kg) | 206000 | N/A | 2.14 | 4.54E-01 | 455000 | 2.99 |

TABLE 20-continued

Compound I Plasma Concentrations of 20 mg/kg of Compound I in Combination with 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| r.p. # 9.6 (Biapenem & Compound I 20 mg/kg) | 102000 | N/A | 2.14 | 2.32E−01 | 441000 | 1.51 |
| r.p. # 9.7 (Biapenem & Compound I 20 mg/kg) | 65100 | N/A | 2.15 | 1.46E−01 | 445000 | 0.948 |
| r.p. # 9.8 (Biapenem & Compound I 20 mg/kg) | 4090 | N/A | 2.14 | 8.96E−03 | 457000 | 0.0451 |
| r.p. # 9.9 (Biapenem & Compound I 20 mg/kg) | 1720 | N/A | 2.14 | 3.92E−03 | 439000 | 0.0121 |
| r.p. # 9.10 (Biapenem & Compound I 20 mg/kg) | 13900 | N/A | 2.14 | 3.13E−02 | 443000 | 0.191 |
| r.p. # 9.10 (Biapenem & Compound I 20 mg/kg) | 330 | N/A | 2.11 | 7.44E−04 | 444000 | <0 |

TABLE 21

Biapenem Plasma Standard Curve of 20 mg/kg of Compound I in Combination with 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| 0.01 ug/mL Biapenem & Compound I in rat r.p.. | 711 | N/A | 2.13 | 5.01E−03 | 142000 | 0.0193 |
| 0.02 ug/mL Biapenem & Compound I in rat r.p.. | 851 | 0.02 | 2.14 | 5.37E−03 | 158000 | 0.0217 |
| 0.05 ug/mL Biapenem & Compound I in rat r.p.. | 1600 | 0.05 | 2.13 | 9.84E−03 | 163000 | 0.0509 |
| 0.1 ug/mL Biapenem & Compound I in rat r.p.. | 2950 | 0.1 | 2.15 | 1.67E−02 | 177000 | 0.0959 |
| 0.2 ug/mL Biapenem & Compound I in rat r.p.. | 6460 | 0.2 | 2.14 | 3.43E−02 | 188000 | 0.211 |
| 0.5 ug/mL Biapenem & Compound I in rat r.p.. | 14700 | 0.5 | 2.14 | 7.72E−02 | 191000 | 0.493 |
| 1 ug/mL Biapenem & Compound I in rat r.p.. | 32900 | 1 | 2.14 | 1.69E−01 | 195000 | 1.09 |
| 2 ug/mL Biapenem & Compound I in rat r.p.. | 66000 | 2 | 2.14 | 3.15E−01 | 209000 | 2.07 |
| 5 ug/mL Biapenem & Compound I in rat r.p.. | 165000 | 5 | 2.14 | 7.94E−01 | 208000 | 5.29 |
| 10 ug/mL Biapenem & Compound I in rat r.p.. | 340000 | 10 | 2.14 | 1.59E+00 | 214000 | 10.8 |
| 20 ug/mL Biapenem & Compound I in rat r.p.. | 647000 | 20 | 2.14 | 2.99E+00 | 216000 | 21.2 |
| 50 ug/mL Biapenem & Compound I in rat r.p.. | 1450000 | 50 | 2.14 | 6.47E+00 | 224000 | 52.5 |
| 100 ug/mL Biapenem & Compound I in rat r.p.. | 2510000 | 100 | 2.14 | 1.05E+01 | 240000 | No Intercept |
| wash | 28500 | N/A | 2.13 | 9.49E+02 | 30 | No Intercept |

TABLE 22

Biapenem Plasma Concentrations of 20 mg/kg of Compound I in Combination with 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| r.p. # 7.1 (Biapenem & Compound I 20 mg/kg) | 74100 | N/A | 0.485 | 9.80E−02 | 756000 | 5.61 |
| r.p. # 7.2 (Biapenem & Compound I 20 mg/kg) | 84600 | N/A | 0.489 | 1.26E−01 | 672000 | 7.98 |

TABLE 22-continued

Biapenem Plasma Concentrations of 20 mg/kg of Compound I
in Combination with 20 mg/kg of Biapenem

| Sample Name | Analyte Peak Area (counts) | Analyte Conc. (ug/mL) | Analyte Retention Time (min) | Area Ratio | IS Peak Area (counts) | Calc. Conc. (ug/mL) |
|---|---|---|---|---|---|---|
| r.p. # 7.3 (Biapenem & Compound I 20 mg/kg) | 64200 | N/A | 0.487 | 9.08E−02 | 708000 | 5.08 |
| r.p. # 7.4 (Biapenem & Compound I 20 mg/kg) | 75800 | N/A | 0.487 | 1.09E−01 | 695000 | 6.47 |
| r.p. # 7.5 (Biapenem & Compound I 20 mg/kg) | 40200 | N/A | 0.486 | 5.87E−02 | 685000 | 3.03 |
| r.p. # 7.6 (Biapenem & Compound I 20 mg/kg) | 27300 | N/A | 0.488 | 3.81E−02 | 718000 | 1.89 |
| r.p. # 7.7 (Biapenem & Compound I 20 mg/kg) | 17600 | N/A | 0.487 | 2.52E−02 | 698000 | 1.22 |
| r.p. # 7.8 (Biapenem & Compound I 20 mg/kg) | 1570 | N/A | 0.486 | 2.29E−03 | 684000 | 0.103 |
| r.p. # 7.9 (Biapenem & Compound I 20 mg/kg) | 516 | N/A | 0.478 | 7.63E−04 | 675000 | 0.0321 |
| r.p. # 7.10 (Biapenem & Compound I 20 mg/kg) | 1520 | N/A | 0.488 | 2.21E−03 | 688000 | 0.100 |
| r.p. # 7.10 (Biapenem & Compound I 20 mg/kg) | 18 | N/A | 0.461 | 2.53E−05 | 693000 | <0 |
| r.p. # 8.1 (Biapenem & Compound I 20 mg/kg) | 54500 | N/A | 0.488 | 8.08E−02 | 674000 | 4.40 |
| r.p. # 8.2 (Biapenem & Compound I 20 mg/kg) | 63000 | N/A | 0.49 | 9.26E−02 | 680000 | 5.21 |
| r.p. # 8.3 (Biapenem & Compound I 20 mg/kg) | 78500 | N/A | 0.493 | 1.18E−01 | 662000 | 7.28 |
| r.p. # 8.4 (Biapenem & Compound I 20 mg/kg) | 36600 | N/A | 0.489 | 5.31E−02 | 691000 | 2.71 |
| r.p. # 8.5 (Biapenem & Compound I 20 mg/kg) | 25600 | N/A | 0.494 | 3.77E−02 | 678000 | 1.87 |
| r.p. # 8.6 (Biapenem & Compound I 20 mg/kg) | 21700 | N/A | 0.487 | 3.11E−02 | 697000 | 1.52 |
| r.p. # 8.7 (Biapenem & Compound I 20 mg/kg) | 12000 | N/A | 0.492 | 1.74E−02 | 693000 | 0.828 |
| r.p. # 8.8 (Biapenem & Compound I 20 mg/kg) | 548 | N/A | 0.481 | 8.33E−04 | 658000 | 0.0353 |
| r.p. # 8.9 (Biapenem & Compound I 20 mg/kg) | 623 | N/A | 0.479 | 9.17E−04 | 679000 | 0.0393 |
| r.p. # 8.10 (Biapenem & Compound I 20 mg/kg) | 886 | N/A | 0.487 | 1.33E−03 | 664000 | 0.0587 |
| r.p. # 8.10 (Biapenem & Compound I 20 mg/kg) | 0 | N/A | 0 | 0.00E+00 | 620000 | No Peak |
| r.p. # 9.1 (Biapenem & Compound I 20 mg/kg) | 51500 | N/A | 0.487 | 7.24E−02 | 712000 | 3.86 |
| r.p. # 9.2 (Biapenem & Compound I 20 mg/kg) | 83800 | N/A | 0.491 | 1.19E−01 | 703000 | 7.34 |
| r.p. # 9.3 (Biapenem & Compound I 20 mg/kg) | 89400 | N/A | 0.487 | 1.37E−01 | 653000 | 9.20 |
| No Sample | N/A | N/A | N/A | N/A | N/A | N/A |
| r.p. # 9.5 (Biapenem & Compound I 20 mg/kg) | 56100 | N/A | 0.49 | 8.82E−02 | 636000 | 4.90 |
| r.p. # 9.6 (Biapenem & Compound I 20 mg/kg) | 29000 | N/A | 0.487 | 4.31E−02 | 672000 | 2.16 |
| r.p. # 9.7 (Biapenem & Compound I 20 mg/kg) | 24000 | N/A | 0.486 | 3.44E−02 | 697000 | 1.69 |
| r.p. # 9.8 (Biapenem & Compound I 20 mg/kg) | 1080 | N/A | 0.488 | 1.59E−03 | 681000 | 0.0705 |
| r.p. # 9.9 (Biapenem & Compound I 20 mg/kg) | 100 | N/A | 0.494 | 1.49E−04 | 670000 | 0.00349 |
| r.p. # 9.10 (Biapenem & Compound I 20 mg/kg) | 2960 | N/A | 0.494 | 4.26E−03 | 694000 | 0.196 |
| r.p. # 9.10 (Biapenem & Compound I 20 mg/kg) | 10 | N/A | 0.483 | 1.51E−05 | 660000 | <0 |

Example 4

The evaluation of Compound I in combination with the carbapenem antibiotic Biapenem against multi-drug resistant strains of Enterobacteriaceae, including those producing serine carbapenemases were also conducted. Antibiotic potentiation activity of Compound I was studied in checkerboard MIC experiments and time-kill assays. The MICs of Biapenem were determined alone or in combination with Compound I added at fixed concentrations between 0.5 and 16 ug/ml) against characterized and engineered isolates producing various beta-lactamases, as well as in geographically diverse panels of multi-drug resistant strains of Enterobacteriaceae (including strains that express the most relevant beta-lactamases).

Biapenem MICs against KPC-producing strains including those expressing multiple classes of enzymes ranged between 8 and 64 µg/ml. The addition of Compound I was associated with marked potentiation in characterized strains of Enterobacteriaceae with serine carbapenemases; Biapenem MICs were <0.25 µg/ml in the presence of 0.3 to 5 µg/ml of Compound I. Time-kill studies in KPC-producing strains (Biapenem MICs of 16-32 ug/ml) demonstrated significant bactericidal synergism by the addition of Compound I. In the multi-drug resistant isolate panel of Enterobacteriaceae (MIC90>32 for fluoroquinolones, aminoglycosides, cephalosporins, aztreonam and pip/tazo), the MIC90 of Biapenem (with 4 ug/ml Compound I) was 0.5 ug/ml. Biapenem showed potency similar to meropenem against *P. aeruginosa*, with no enhancement with the addition of Compound I. The results suggest that Compound I combined with the carbapenem Biapenem is a highly active against Gram-negative pathogens, particularly against carbapenem-resistant Enterobacteriaceae and serine carbapenemases such as KPC.

Example 5

Example 5 provides the single-dose pharmacokinetic studies of Compound I inpreclinical species, including intraperitoneal administration to Swiss-Webster mice and intravaneous administration to Sprague-Dawley rats, Beagle dogs, and Cynomologus monkeys.

Intravaneous doses of Compound I were administered as 30-minute infusions. The pharmacokinetics of Compound I were also studied with coadministration of the carbapenem, Biapenem. Compound I concentrations were determined using an LC-MS detection method.

The mean pharmacokinetic parameters for Compound I are shown in Table 23 below. Compound I showed linear and favorable pharmacokinetic properties across all species, with clearance and volume of distribution comparable to those reported for beta-lactam antibiotics in these species. Clearance and volume of distribution were independent of dose. No PK drug interactions between Compound I and Biapenem were observed.

TABLE 23

Pharmacokinetics Studies of Preclinical Species

| Species | Dose (mg/kg)/ Route | $C_{max}$ (µg/mL) | AUC (µg · h/mL) | CL or CL/F (L/kg/h) | $V_{ss}$ or $V_{ss}/F$ (L/kg) | $T_{1/2}$ (h) |
|---|---|---|---|---|---|---|
| Mouse | 5 IP | 8.26 | 3.1 | 1.61 | 0.38 | 0.16 |
| Mouse | 15 IP | 19.50 | 8.30 | 1.80 | 0.50 | 0.20 |
| Mouse | 50 IP | 67.09 | 31.35 | 1.60 | 0.60 | 0.25 |
| Rat | 20 IV | 19.8 ± 0.84 | 12.2 ± 0.43 | 1.7 ± 0.06 | 0.79 ± 0.07 | 1.6 ± 0.17 |
| Rat | 50 IV | 45.9 ± 2.00 | 28.2 ± 2.0 | 1.8 ± 0.13 | 1.31 ± 0.37 | 4.5 ± 1.34 |
| Dog | 2 IV | 6.49 ± 0.31 | 6.13 ± 0.65 | 0.33 ± 0.03 | 0.25 ± 0.02 | 0.66 ± 0.06 |
| Dog | 6 IV | 19.56 ± 1.42 | 18.39 ± 2.36 | 0.33 ± 0.04 | 0.26 ± 0.01 | 0.71 ± 0.09 |
| Dog | 20 IV | 66.79 ± 6.16 | 73.64 ± 5.38 | 0.27 ± 0.02 | 0.27 ± 0.03 | 1.53 ± 0.73 |
| Monkey | 2 IV | 5.35 ± 0.28 | 3.96 ± 0.51 | 0.51 ± 0.07 | 0.26 ± 0.01 | 0.57 ± 0.03 |
| Monkey | 6 IV | 17.04 ± 1.68 | 12.19 ± 1.89 | 0.50 ± 0.08 | 0.24 ± 0.01 | 0.55 ± 0.12 |
| Monkey | 20 IV | 54.89 ± 3.32 | 41.84 ± 2.53 | 0.48 ± 0.03 | 0.26 ± 0.03 | 1.89 ± 1.73 |

Example 6

Example 6 provides the in vivo efficacy study of the carbapenem Biapenem in combination with Compound I in mouse models of pulmonary and thigh infection due to the carbapenem-resistant, KPC-producing *K. pneumoniae*.

Four *K. pneumoniae* strains with Biapenem MICs ranging between 0.25-64 mg/L were used. Neutropenic mice were infected with ~$10^5$ CFU/lung or ~$10^6$ CFU/thigh. Intraperitoneal treatments with 50 mpk Biapenem+/−50 mpk Compound I were initiated 2 hours post-infection as a single dose or continued every two hours for 24 hours. Mice were sacrificed on designated time points and colony counts in tissue determined.

In KPC-producing strains, treatment with Biapenem/Compound I produced significantly lower bacterial counts in tissues compared to Biapenem alone groups in both infection models. In lung infection, the extent of bacterial killing after an hour of a single dose was up to 1.3 log CFU greater than that in the control (Biapenem alone) group. The thigh infection model data is shown in Table 24 below. Treatment with Biapenem/Compound I produced significant bacterial killing in both the murine thigh and lung infection models using strains resistant to Biapenem treatment. These data show this combination to be a promising therapeutic option for the treatment of infections caused by KPC producing strains.

TABLE 24

In vivo Efficacy of Biapenem/Compound I Combination

| | Biapenem MIC (µg/mL) | | Change |
|---|---|---|---|
| Strain | Alone | with Compound I (5 µg/mL) | Compound | in Log CFU/thigh ± SD @ 24 h |
| ATCC 43816 | 0.25 | 0.25 | Biapenem | −1.09 ± 0.30 |
| | | | Biapenem + Compound I | −1.33 ± 0.41 |

TABLE 24-continued

In vivo Efficacy of Biapenem/Compound I Combination

| | Biapenem MIC (µg/mL) | | | Change in Log CFU/thigh ± SD @ 24 h |
|---|---|---|---|---|
| Strain | Alone | with Compound I (5 µg/mL) | Compound | |
| KP1004 | 16 | ≤0.06 | Biapenem | +0.71 ± 0.10 |
| | | | Biapenem + Compound I | −0.91 ± 0.15 |
| KP1061 | 32 | ≤0.06 | Biapenem | +1.67 ± 0.09 |
| | | | Biapenem + Compound I | −0.69 ± 0.09 |
| KP1074 | 64 | 0.25 | Biapenem | +0.98 ± 0.46 |
| | | | Biapenem + Compound I | −1.25 ± 0.24 |

What is claimed is:

1. A method for treating a bacterial infection in a human, comprising administering to a subject in need thereof a composition comprising Compound I or a pharmaceutically acceptable salt thereof and a carbapenem antibacterial agent to achieve a Compound I plasma clearance from about 0.01 L/h/kg to about 5 L/h/kg, wherein compound I has the structure:

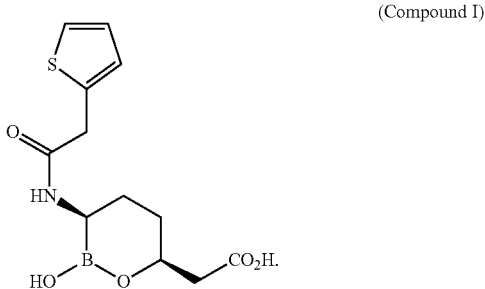 [SMILES: O=C(O)C[C@@H]1CC[C@H](NC(=O)Cc2cccs2)B(O)O1]

(Compound I)

2. The method of claim 1, wherein the carbapenem antibacterial agent is selected from the group consisting of Imipenem, Biapenem, Doripenem, Meropenem, and Ertapenem.

3. The method of claim 2, wherein the carbapenem antibacterial agent is Biapenem.

4. The method of claim 1, wherein Compound I is administered in a dose range from about 0.1 mg/kg to about 1,000 mg/kg of body weight.

5. The method of claim 4, wherein Compound I is administered in a dose range from about 0.5 mg/kg to about 500 mg/kg of body weight.

6. The method of claim 1, wherein the Compound I plasma clearance is from about 0.025 L/h/kg to about 2.2 L/h/kg.

7. The method of claim 1, wherein the Compound I plasma clearance is from about 0.05 L/h/kg to about 1 L/h/kg.

8. The method of claim 1, wherein the composition is administered intravenously.

9. The method of claim 1, wherein the infection is caused by a bacteria selected from the group consisting of Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii, and Bacteroides splanchnicus.

10. The method of claim 1, wherein the composition further comprises an additional medicament selected from the group consisting of an antibacterial agent, an antifungal agent, an antiviral agent, an anti-inflammatory agent, and an anti-allergic agent.

11. A method for treating a bacterial infection in a human, comprising administering to a subject in need thereof a composition comprising Compound I or a pharmaceutically acceptable salt thereof and a carbapenem antibacterial agent to achieve a Compound I half-life from about 0.05 hr to about 10 hrs, wherein Compound I has the structure:

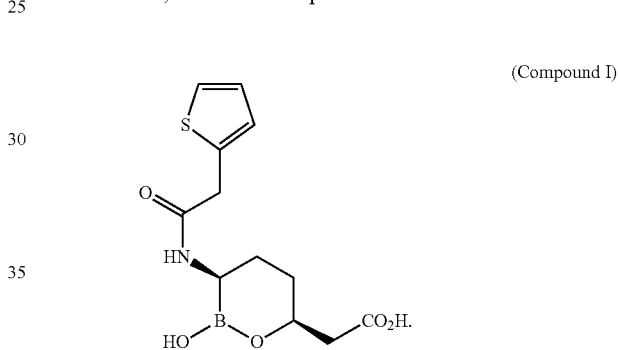

(Compound I)

12. The method of claim 11, wherein the carbapenem antibacterial agent is selected from the group consisting of Imipenem, Biapenem, Doripenem, Meropenem, and Ertapenem.

13. The method of claim 12, wherein the carbapenem antibacterial agent is Biapenem.

14. The method of claim 11, wherein Compound I is administered in a dose range from about 0.1 mg/kg to about 1,000 mg/kg of body weight.

15. The method of claim 14, wherein Compound I is administered in a dose range from about 0.5 mg/kg to about 500 mg/kg of body weight.

16. The method of claim 11, wherein the Compound I half-life is from about 0.1 hr to about 7 hrs.

17. The method of claim 11, wherein the Compound I half-life is from about 0.3 hr to about 5 hrs.

18. The method of claim 11, wherein the composition is administered intravenously.

19. The method of claim 11, wherein the infection is caused by a bacteria selected from the group consisting of Pseudomonas aeruginosa, Pseudomonas fluorescens, Stenotrophomonas maltophilia, Escherichia coli, Citrobacter freundii, Salmonella typhimurium, Salmonella typhi, Salmonella paratyphi, Salmonella enteritidis, Shigella dysenteriae, Shigella flexneri, Shigella sonnei, Enterobacter cloacae, Enterobacter aerogenes, Klebsiella pneumoniae, Klebsiella oxytoca, Serratia marcescens, Acinetobacter calcoaceticus, Acinetobacter haemolyticus, Yersinia enterocolitica, *Yersinia pestis, Yersinia pseudotuberculosis, Yersinia intermedia, Haemophilus influenzae, Haemophilus parainfluenzae, Haemophilus haemolyticus, Haemophilus parahaemolyticus, Helicobacter pylori, Campylobacter fetus, Campylobacter jejuni, Campylobacter coli, Vibrio cholerae, Vibrio parahaemolyticus, Legionella pneumophila, Listeria monocytogenes, Neisseria gonorrhoeae, Neisseria meningitidis, Moraxella, Bacteroides fragilis, Bacteroides vulgatus, Bacteroides ovalus, Bacteroides thetaiotaomicron, Bacteroides uniformis, Bacteroides eggerthii*, and *Bacteroides splanchnicus*.

20. The method of claim 11, wherein the composition further comprises an additional medicament selected from the group consisting of an antibacterial agent, an antifungal agent, an antiviral agent, an anti-inflammatory agent, and an anti-allergic agent.

\* \* \* \* \*